United States Patent
Mackovic Basic et al.

(10) Patent No.: US 10,010,345 B2
(45) Date of Patent: Jul. 3, 2018

(54) INSTRUMENT FOR OCCLUSION OF UTERINE BLOOD VESSELS

(71) Applicants: Miriam Mackovic Basic, Rancho Palos Verdes, CA (US); Mario Basic, Rancho Palos Verdes, CA (US); Arkadiy Royzen, Brooklyn, NY (US); Zinovy Royzen, Seattle, WA (US)

(72) Inventors: Miriam Mackovic Basic, Rancho Palos Verdes, CA (US); Mario Basic, Rancho Palos Verdes, CA (US); Arkadiy Royzen, Brooklyn, NY (US); Zinovy Royzen, Seattle, WA (US)

( * ) Notice: Subject to any disclaimer, the term of this patent is extended or adjusted under 35 U.S.C. 154(b) by 132 days.

(21) Appl. No.: 13/986,218

(22) Filed: Apr. 15, 2013

(65) Prior Publication Data

US 2014/0309671 A1    Oct. 16, 2014
US 2017/0000525 A9    Jan. 5, 2017

Related U.S. Application Data

(62) Division of application No. 13/066,065, filed on Apr. 5, 2011, now Pat. No. 8,465,496.
(Continued)

(51) Int. Cl.
*A61B 17/44*    (2006.01)
*A61B 17/42*    (2006.01)
(Continued)

(52) U.S. Cl.
CPC .............. *A61B 17/42* (2013.01); *A61B 17/12* (2013.01); *A61B 17/28* (2013.01);
(Continued)

(58) Field of Classification Search
CPC ..... A61B 17/12; A61B 17/122; A61B 17/128; A61B 17/28; A61B 17/2812;
(Continued)

(56) References Cited

U.S. PATENT DOCUMENTS 818,953 A *   4/1906   Gottlieb ..................... 606/126
2,637,320 A *   5/1953   Greenberg ................. 606/122
(Continued)

*Primary Examiner* — Ryan J Severson
(74) *Attorney, Agent, or Firm* — Omni Legal Group; Omid E. Khalifeh

(57) ABSTRACT

A surgical instrument for at least partial occlusion of the uterus blood vessels comprising two opposing jaws with scissor-type handles and a latching mechanism.

Each jaw has a straight member 1 and a straight member 2 connected with an angle 30-45 degrees. Each said member 1 has a tubular cover. Each member 2 is integrated with the scissor-type handle. Each jaw has an inner side and an outer side. The jaws are made movable relative to each other in order to at least partially occlude the uterus blood vessels by the opposite sides of the covers on the inner sides of the members 1.

The latching mechanism is made to retain the jaws in the working position over a needed period of time and release the jaws when the need for occlusion is over.

Each cover has an inner cavity open from one end for receiving and retaining the member 1 of said jaw. The thickness of each said cover on the inner side of the member 1 is 8-12 mm, the width of said cover is 10-30 mm, the length of said cover is 50-60 mm, and said cover is made of soft plastic, silicon, fabric, gauze or non woven material.

10 Claims, 38 Drawing Sheets

Related U.S. Application Data

(60) Provisional application No. 61/342,053, filed on Apr. 7, 2010.

(51) Int. Cl.
*A61B 17/12* (2006.01)
*A61B 17/28* (2006.01)

(52) U.S. Cl.
CPC ............... *A61B 2017/2808* (2013.01); *A61B 2017/2825* (2013.01); *A61B 2017/2829* (2013.01)

(58) Field of Classification Search
CPC .............. A61B 17/2816; A61B 17/282; A61B 17/2833; A61B 17/2841; A61B 17/42; A61B 17/4241; A61B 17/44; A61B 2017/0042; A61B 2017/0078; A61B 2017/12004; A61B 2017/2825; A61B 2017/2829; A61B 2017/2837; A61B 2017/4216; A61B 2017/4233; A61B 2017/445; A61B 2017/447

See application file for complete search history.

(56) References Cited

U.S. PATENT DOCUMENTS

| | | | | |
|---|---|---|---|---|
| 2,743,726 | A * | 5/1956 | Grieshaber | 606/207 |
| 2,755,806 | A * | 7/1956 | Greenberg | 606/122 |
| 3,446,211 | A * | 5/1969 | Markham | A61B 17/2812 606/207 |
| 3,503,396 | A * | 3/1970 | Pierie | A61B 17/282 24/517 |
| 3,503,397 | A * | 3/1970 | Raible | A61B 17/282 24/517 |
| 3,503,398 | A * | 3/1970 | Raible | A61B 17/282 606/207 |
| 3,779,248 | A * | 12/1973 | Karman | 606/207 |
| 3,921,641 | A * | 11/1975 | Hulka | 606/208 |
| 4,120,302 | A * | 10/1978 | Ziegler | 606/207 |
| 4,226,240 | A * | 10/1980 | Walker, Jr. | 606/207 |
| 4,452,244 | A * | 6/1984 | Chin | 606/209 |
| 4,821,719 | A * | 4/1989 | Fogarty | 606/158 |
| 4,834,090 | A * | 5/1989 | Moore | 606/148 |
| 5,036,733 | A * | 8/1991 | Tiholiz et al. | 76/119 |
| 5,037,430 | A * | 8/1991 | Hasson | 606/119 |
| 5,250,072 | A * | 10/1993 | Jain | 606/205 |
| 5,514,147 | A * | 5/1996 | Hoskin et al. | 606/151 |
| 5,891,017 | A * | 4/1999 | Swindle et al. | 600/205 |
| 5,902,312 | A * | 5/1999 | Frater et al. | 606/148 |
| 5,922,008 | A * | 7/1999 | Gimpelson | 606/207 |
| 6,007,552 | A * | 12/1999 | Fogarty et al. | 606/157 |
| 6,013,088 | A * | 1/2000 | Karavidas | 606/157 |
| 6,099,539 | A * | 8/2000 | Howell et al. | 606/151 |
| 6,165,186 | A * | 12/2000 | Fogarty et al. | 606/157 |
| 6,206,896 | B1 * | 3/2001 | Howell et al. | 606/151 |
| 6,228,104 | B1 * | 5/2001 | Fogarty et al. | 606/207 |
| 6,254,601 | B1 * | 7/2001 | Burbank et al. | 606/45 |
| 6,273,902 | B1 * | 8/2001 | Fogarty et al. | 606/207 |
| 6,293,954 | B1 * | 9/2001 | Fogarty et al. | 606/151 |
| 6,299,621 | B1 * | 10/2001 | Fogarty et al. | 606/151 |
| 6,312,445 | B1 * | 11/2001 | Fogarty et al. | 606/207 |
| 6,375,611 | B1 * | 4/2002 | Voss et al. | 600/210 |
| 6,387,106 | B1 * | 5/2002 | Howell et al. | 606/151 |
| 6,387,112 | B1 * | 5/2002 | Fogarty et al. | 606/207 |
| 6,461,368 | B2 * | 10/2002 | Fogarty et al. | 606/151 |
| 6,530,942 | B2 * | 3/2003 | Fogarty et al. | 606/207 |
| 6,550,482 | B1 * | 4/2003 | Burbank et al. | 128/898 |
| 6,558,408 | B1 * | 5/2003 | Fogarty et al. | 606/207 |
| 6,579,304 | B1 * | 6/2003 | Hart et al. | 606/207 |
| 6,626,922 | B1 * | 9/2003 | Hart et al. | 606/157 |
| 6,692,514 | B2 * | 2/2004 | Fogarty et al. | 606/207 |
| 6,719,766 | B1 * | 4/2004 | Buelna et al. | 606/151 |
| 6,849,044 | B1 * | 2/2005 | Voss et al. | 600/229 |
| 6,905,506 | B2 * | 6/2005 | Burbank | A61B 5/415 600/504 |
| 6,932,825 | B2 * | 8/2005 | Anderson | 606/147 |
| 6,942,676 | B2 * | 9/2005 | Buelna | 606/158 |
| 6,989,017 | B2 * | 1/2006 | Howell et al. | 606/151 |
| 7,048,744 | B2 * | 5/2006 | Wiess | A61B 1/303 600/231 |
| 7,117,873 | B2 * | 10/2006 | Bachrach | A45D 24/30 132/129 |
| 7,172,603 | B2 * | 2/2007 | Burbank | A61B 17/1227 606/119 |
| 7,207,996 | B2 * | 4/2007 | Burbank et al. | 606/151 |
| 7,223,279 | B2 * | 5/2007 | Burbank et al. | 606/205 |
| 7,229,465 | B2 * | 6/2007 | Burbank | A61B 5/415 600/504 |
| 7,297,104 | B2 * | 11/2007 | Vanden Hoek et al. | 600/37 |
| 7,329,265 | B2 * | 2/2008 | Burbank et al. | 606/157 |
| 7,594,890 | B2 * | 9/2009 | Burbank | A61B 5/415 600/439 |
| 7,645,284 | B2 * | 1/2010 | Burbank et al. | 606/139 |
| 7,651,511 | B2 * | 1/2010 | Burbank et al. | 606/158 |
| 7,744,623 | B2 * | 6/2010 | Anderson | 606/207 |
| 7,819,860 | B2 * | 10/2010 | Wittenberger et al. | 606/23 |
| 7,824,425 | B2 * | 11/2010 | Biolchini, Jr. | 606/208 |
| 7,955,325 | B2 * | 6/2011 | Wittenberger et al. | 606/23 |
| 8,092,473 | B2 * | 1/2012 | Hart et al. | 606/157 |
| 8,273,102 | B2 * | 9/2012 | Danitz et al. | 606/207 |
| 8,465,496 | B2 * | 6/2013 | Mackovic Basic et al. | 606/119 |
| 8,556,913 | B2 * | 10/2013 | Varma | A61B 17/42 606/122 |
| 8,740,933 | B2 * | 6/2014 | Anderson | 606/207 |
| 9,055,973 | B2 * | 6/2015 | Varma | A61B 17/42 |
| 9,089,355 | B2 * | 7/2015 | Hermann | A61B 17/122 |
| 9,113,939 | B2 * | 8/2015 | Strokosz | A61B 17/2909 |
| 2001/0029390 | A1 * | 10/2001 | Fogarty et al. | 606/207 |
| 2002/0049470 | A1 * | 4/2002 | Fogarty et al. | 606/205 |
| 2002/0111650 | A1 * | 8/2002 | Fogarty et al. | 606/207 |
| 2002/0165579 | A1 * | 11/2002 | Burbank et al. | 606/205 |
| 2002/0177842 | A1 * | 11/2002 | Weiss | 606/1 |
| 2002/0183770 | A1 * | 12/2002 | Anderson | 606/157 |
| 2002/0183771 | A1 * | 12/2002 | Burbank et al. | 606/158 |
| 2002/0183785 | A1 * | 12/2002 | Howell et al. | 606/207 |
| 2002/0188306 | A1 * | 12/2002 | Burbank et al. | 606/151 |
| 2003/0093113 | A1 * | 5/2003 | Fogarty et al. | 606/207 |
| 2003/0120306 | A1 * | 6/2003 | Burbank et al. | 606/205 |
| 2003/0181932 | A1 * | 9/2003 | Buelna | 606/158 |
| 2003/0191391 | A1 * | 10/2003 | Burbank et al. | 600/453 |
| 2003/0236537 | A1 * | 12/2003 | Hart et al. | 606/151 |
| 2004/0097962 | A1 * | 5/2004 | Burbank et al. | 606/119 |
| 2004/0153105 | A1 * | 8/2004 | Burbank et al. | 606/157 |
| 2004/0167552 | A1 * | 8/2004 | Buelna et al. | 606/158 |
| 2004/0254606 | A1 * | 12/2004 | Wittenberger et al. | 606/205 |
| 2005/0059987 | A1 * | 3/2005 | Hermann et al. | 606/157 |
| 2005/0059988 | A1 * | 3/2005 | Danitz et al. | 606/157 |
| 2005/0101974 | A1 * | 5/2005 | Burbank et al. | 606/151 |
| 2005/0192474 | A1 * | 9/2005 | Vanden Hoek et al. | 600/37 |
| 2005/0192605 | A1 * | 9/2005 | Hart et al. | 606/157 |
| 2005/0240219 | A1 * | 10/2005 | Kahle et al. | 606/207 |
| 2005/0245947 | A1 * | 11/2005 | Harmanli | 606/157 |
| 2005/0251184 | A1 * | 11/2005 | Anderson | 606/157 |
| 2006/0074328 | A1 * | 4/2006 | Burbank et al. | 600/504 |
| 2006/0190033 | A1 * | 8/2006 | Molloy | 606/205 |
| 2007/0149969 | A1 * | 6/2007 | Wittenberger et al. | 606/48 |
| 2007/0167977 | A1 * | 7/2007 | Biolchini, Jr. | 606/205 |
| 2007/0173863 | A1 * | 7/2007 | Burbank et al. | 606/119 |
| 2007/0179526 | A1 * | 8/2007 | Hart et al. | 606/207 |
| 2007/0203505 | A1 * | 8/2007 | Burbank et al. | 606/119 |
| 2007/0299470 | A1 * | 12/2007 | Vanden Hoek et al. | 606/205 |
| 2008/0154284 | A1 * | 6/2008 | Varma | 606/122 |
| 2008/0200924 | A1 * | 8/2008 | Burbank et al. | 606/119 |
| 2008/0294190 | A1 * | 11/2008 | Young | 606/205 |
| 2008/0300622 | A1 * | 12/2008 | Xu | 606/207 |
| 2010/0256660 | A1 * | 10/2010 | Anderson | 606/157 |
| 2010/0324568 | A1 * | 12/2010 | Varma | 606/121 |
| 2011/0093005 | A1 * | 4/2011 | Strokosz et al. | 606/205 |
| 2011/0208237 | A1 * | 8/2011 | Su | 606/208 |
| 2011/0251622 | A1 * | 10/2011 | Basic et al. | 606/119 |
| 2014/0309671 | A1 * | 10/2014 | Basic et al. | 606/158 |

(56) References Cited

U.S. PATENT DOCUMENTS

* cited by examiner

INSTRUMENT FOR OCCLUSION OF UTERINE BLOOD VESSELS

This application is a divisional application of utility patent application Ser. No. 13/066,065 applied Apr. 5, 2011 and claim benefits of provisional Patent Application U.S. 61/342,053 applied Apr. 7, 2010.

FIELD OF THE INVENTION

The present invention relates to medical instruments and more particularly to the instruments for occlusion of the uterine blood vessels used in performing the surgical operation cesarean section and other surgical procedures.

BACKGROUND OF THE INVENTION

At the present time the cesarean section is one of the most widely used surgical procedures. A cesarean section is a major surgical procedure in which a baby is removed from the uterus by making a cut into the abdomen and then into the uterus. In many cases, a cesarean section is necessary to save the life of the baby or the mother. In other cases, a cesarean section is performed when a vaginal birth is not possible, e.g., failure of normal progression of labor. In some other cases, a cesarean section may be scheduled due to a patient's request, or recommended by another doctor.

The cesarean section begins with an incision or cut on the skin. This cut is carried deeper until the abdomen is completely open (into the peritoneal cavity). The bladder, which is normally attached to the front of the uterus, is released. This is done by cutting the attachments of the bladder to the uterus and pushing it away. A cut is then made in the uterus. This cut is then carried deeper until the uterine wall is completely divided. The uterine incision is then extended by tearing the tissue or cutting it with a sharp scissor. The amniotic cavity, a baby sac with its surrounding fluid ("waters") is opened. The baby is then delivered and handed to the pediatric or baby care team. The after-birth, or placenta, is then removed. The incision is then closed.

One of the biggest problems related to a cesarean section is blood loss. The average blood loss is about 1000 ml. It is about two times larger than during a vaginal delivery. It can cause serious morbidity and mortality and the problem of hemorrhage is well-described in multiple studies.

Every woman would benefit from lower blood loss during a cesarean section. Low blood loss is particularly important in the situations where blood is not available or the patient does not want to accept blood transfusion (like Jehovah witnesses). There are many procedures and instruments developed with intention to correct severe blood loss—most of them used after blood loss occurred.

The methods and instruments used for non-permanent occlusion of uterine arteries are described in U.S. Pat. Nos. 6,254,601, 7,329,265, 7,354,444, and U.S. Pat. Appl. Nos 2006/0178698, 2007/0203505.

A method for performing a cesarean section usually comprising the following steps:
a) skin incision,
b) uterine incision,
c) delivering the baby,
d) delivering placenta,
e) pulling the uterus out from the pelvic cavity and placing the uterus on the patient abdomen,
f) suturing the uterus,
g) closing the patient.

The time of suturing of the uterus depends on the rate of its bleeding. The more uterus incision bleeds, the more time is needed to suck the blood by sponges and suture the uterus. The bleeding has to be stopped so that the surgeon can see clearly the area to be sutured. Even though the time of the suturing of the uterus is relatively short (about 5-10 minutes), the patient could lose a significant amount of blood just during the suturing of the uterus alone.

To stop the bleeding, physicians are currently using the uterine artery occlusion, either temporary or permanent. Permanent occlusion utilizes particles injected in the uterine arteries. It is expensive process, has to be planned in advance and is time consuming. Due to expense and invasive nature of the procedure, it has a very limited application. Placing the uterine artery balloon is a temporary procedure, but is still limited by the cost and invasive nature of the procedure.

There is a known clamp for occlusion of uterine arteries during hysterectomy. Such clamp is shown at TeLinde Operative Gynecology, auth: John A Rock, editor Howard W Jones, publisher: Lippincott Williams & Wilkins, 9th edition, 2003, FIG. 19-13 A-C, page 622.
A. "The ascending branches of the uterine artery are clamped, cut, and suture is placed just below the tip of the clamp and immediately next to the uterine wall.
B. After removing the clamp, the suture is tied, thus securing the vessels before they are cut.
C. The pedicle is regrasped just above the tie and then doubly ligated."

However, these clamps could not be used for occlusion of the uterine arteries during a normal cesarean section where there is no need for a hysterectomy for a number of reasons. The clamp damages the uterine arteries and damage during cesarean section could be life threatening. The profile of the clamp does not fit the abdomen of the patient during cesarean section. Also, during a cesarean section, at the end of pregnancy the uterine vessels are much large than before pregnancy. For example, the width of both an artery and vein exposed after pulling the uterus out from the pelvic cavity and placing the uterus on the patient abdomen can be 40 mm or even more. Since it is difficult to occlude an artery only, the clamp has to occlude both the uterine artery and the vein which goes along the artery. There is no clamp which could do it without damaging the blood vessels. Therefore, there is a need for a simple, convenient, fast, harmless for a fetus and the blood vessels, inexpensive method and instrument that can be applied right during the cesarean section surgery that would significantly reduce blood loss.

SUMMARY OF THE INVENTION

The present invention is directed to a device for reducing blood loss during cesarean section. The method for performing a cesarean section is comprised of the following steps:
a) skin incision,
b) uterine incision,
c) delivering the baby,
d) delivering placenta,
e) pulling the uterus out from the pelvic cavity and placing the uterus on the patient abdomen, and exposing the uterine, arteries,
f) applying pressure on at least one of the two exposed uterine arteries for its at least partial occlusion by an atraumatic occlusion instrument,
g) suturing the uterus,
h) removing the occlusion instrument or instruments,
g) closing the patient.

A surgical instrument for at least partially occlusion of the uterus blood vessels comprising two jaws movable relative to each other to at least partially occlude the uterus blood vessels, latching mechanism to retain the jaws the in the working position over needed period of time and release the jaws when the need for occlusion is over, a disposable tubular cover on the end member of each jaw, said end member of a jaw is connected with the other member of the jaw with an angle 25-45 degrees, preferred angle is 30-45 degrees, said cover has an inner cavity open from one end for receiving and retaining the jaw, the thickness of the side of the cover to be engaged with the blood vessels is 3-15 mm, preferably, 8-12 mm, the width of said cover is 10-30 mm, the length of said cover is 50-60 mm, and said cover made of gauze or fabric.

In another embodiment, a disposable cover for a surgical instrument having two jaws for at least partially occlusion of blood vessels, comprising a tubular body having two parts connected along their three sides, said connection defines an inner space between said parts open from one end for receiving and retaining the jaw, said parts are made of soft plastic or silicon.

DETAILED DESCRIPTION OF THE PREFERRED EMBODIMENT

In accordance with a first exemplary embodiment of the present invention, an instrument for occlusion of the uterine blood vessels is used during performing a Cesarean section including the following steps:
a) skin incision,
b) uterine incision,
c) delivering the baby,
d) delivering placenta,
e) pulling the uterus out from the pelvic cavity and placing the uterus on the patient abdomen, and exposing the uterine arteries,
f) applying pressure on at least one of the two exposed uterine arteries or an artery and the vein along it for at least partial occlusion by an atraumatic occlusion instrument, for example an atraumatic clamp,
g) suturing the uterus,
h) removing the occlusion instrument or instruments,
g) closing the patient.
Steps a-d are well known.

Simultaneously with application of pressure on at least one of the two exposed uterine arteries by an atraumatic occlusion instrument, the pressure is also applied on the vein adjacent to the said artery by the same atraumatic occlusion instrument.

Figure 1:
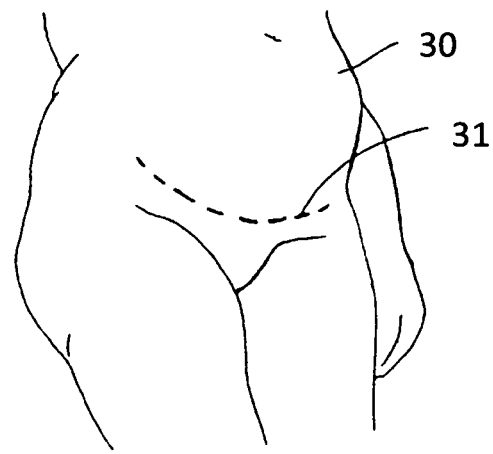
FIG. 1 is a perspective view of the transverse incision in the abdominal wall in a cesarean section.
Figure 2:
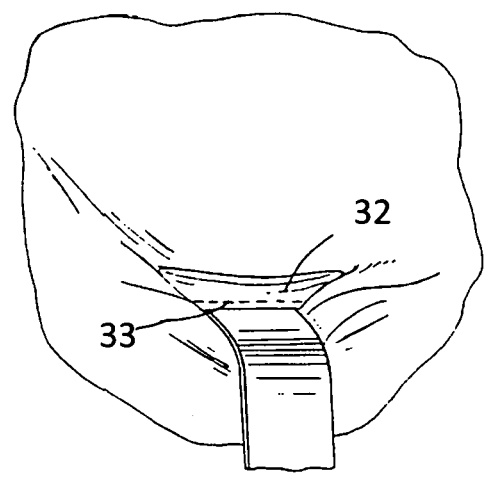
FIG. 2 is a perspective view of the uterus.

In the cesarean section procedure of the present invention, the patient 30, FIG. 1, is partially or fully anesthetized. A transverse incision (cut) 31 is made through the wall of the abdomen. The vesicouterine fold is then opened and the bladder is retracted, as seen in FIG. 2. After that, a transverse incision 32 is made through the wall of the uterus along incision line 33. The baby and placenta are then delivered. After that, the uterus round ligament 35 is pulled from the pelvic cavity and placed on the patient abdomen exposing the uterine blood vessels 36 and 37. It is more convenient to suture the uterus when the round ligament is placed on the patient abdomen.

Figure 3:
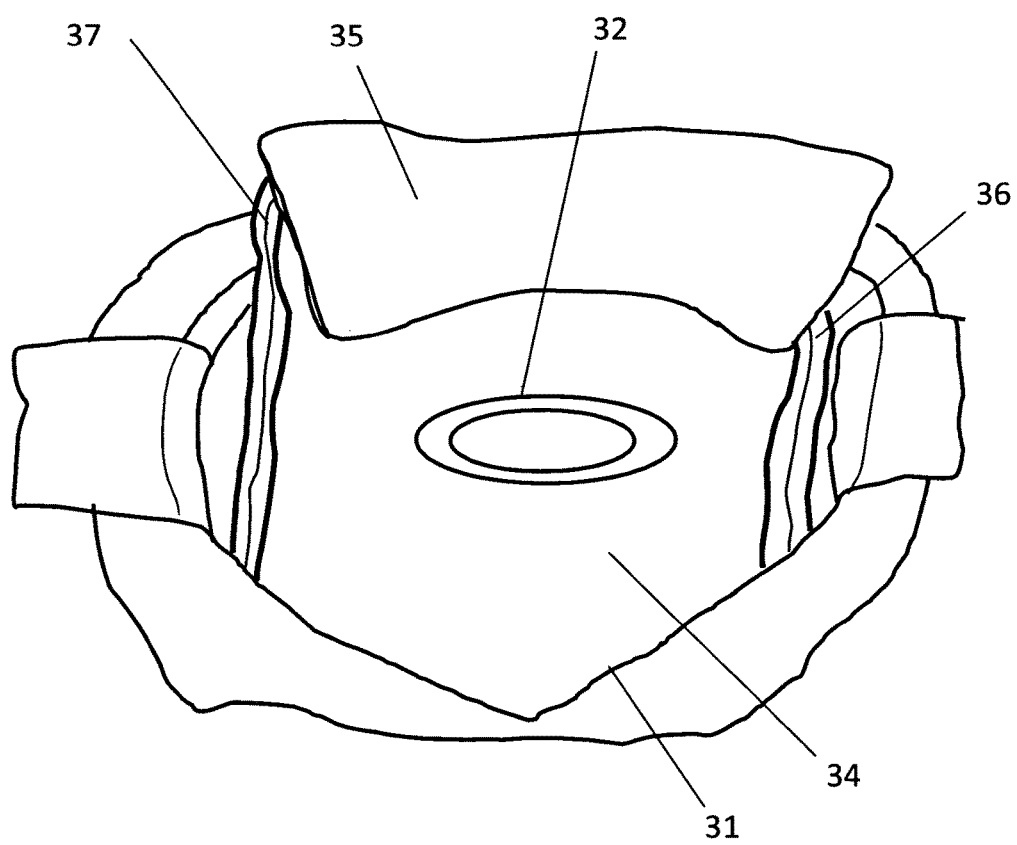
FIG. 3 is a top view of the incision after the uterus was placed on the patient abdomen, and the uterine arteries are exposed.

FIG. 3 is a top view of the incision after the uterus round ligament 35 was placed on the patient abdomen, and the uterine vessels 36 and 37 are exposed. Each set of vessels 36 and 37 includes a uterine artery and a vein. These steps are conventional steps in performing cesarean section surgeries and they are used in the invention as well.

Next conventional step in prior art is to suture the incision 32 of the uterus 34. The time of suturing of the incision 32 depends on the rate of its bleeding. The more uterus incision 32 is bleeding, the more time is needed to suck the blood by sponges and suture the uterus. The bleeding has to be stopped so that the surgeon could see clearly the area to be sutured. Even though the time of the suturing of the uterus is relatively short (about 5-10 minutes), the patient could loss a significant amount of blood just during the suturing of the uterus alone.

Before suturing the incision 32 of the uterus 34 the uterus vessels 36 and 37 are occluded with atraumatic instruments, for example atramautic clamps 38. The word "clamp" will refer to the occlusion instruments which have opposing jaws.

The atraumatic clamps are applied immediately after the baby is delivered and uterus round ligament 35 was placed on the patient abdomen. In the present invention the uterus round ligament 35 is placed on the patient abdomen immediately after the baby was delivered in order to occlude the uterine blood vessels 36 and 37 as quickly as possible.

In most cases, the occlusion of a uterine artery includes also occlusion of the vein although it is not necessary. This happens because the artery and the vein are close to each other. This is why we referenced to this step as the occlusion of the uterine vessels 36 and 37 even though there is a need to occlude the uterine arteries only. It is possible to occlude just one uterine artery (one set of uterine vessels, for example, vessels 37 occluded by a clamp 38) in order to reduce bleeding of the incision 32, as shown on FIG. 4. However, the occlusion of the both uterine arteries (vessels 36 and 37), as shown on FIG. 5, are preferred. The uterine vessels 36 and 37 are occluded by pressure applied from outside of the vessels by occlusion instruments, for example, the atraumatic clamps 38. The occlusion instruments have to be atraumatic in order to eliminate any possible damage to the uterine arteries.

Figure 4:
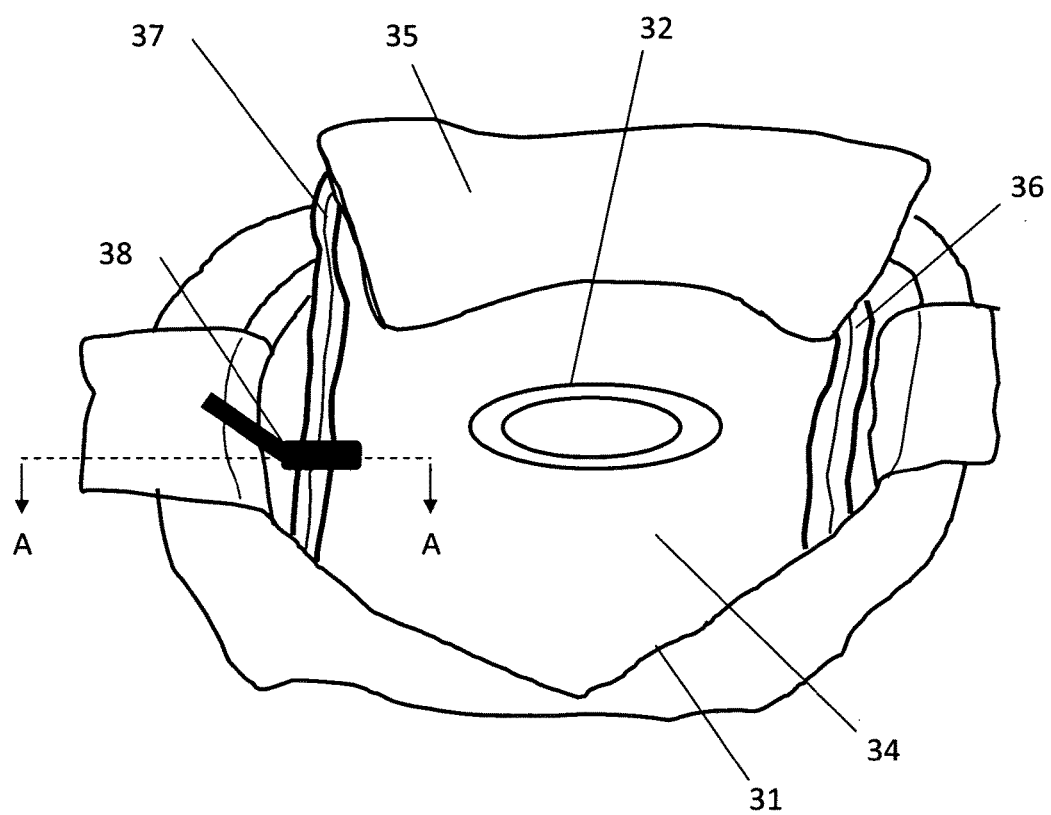
FIG. 4 is a top view of the incision after the atraumatic occlusion instrument is applied.
Figure 5:
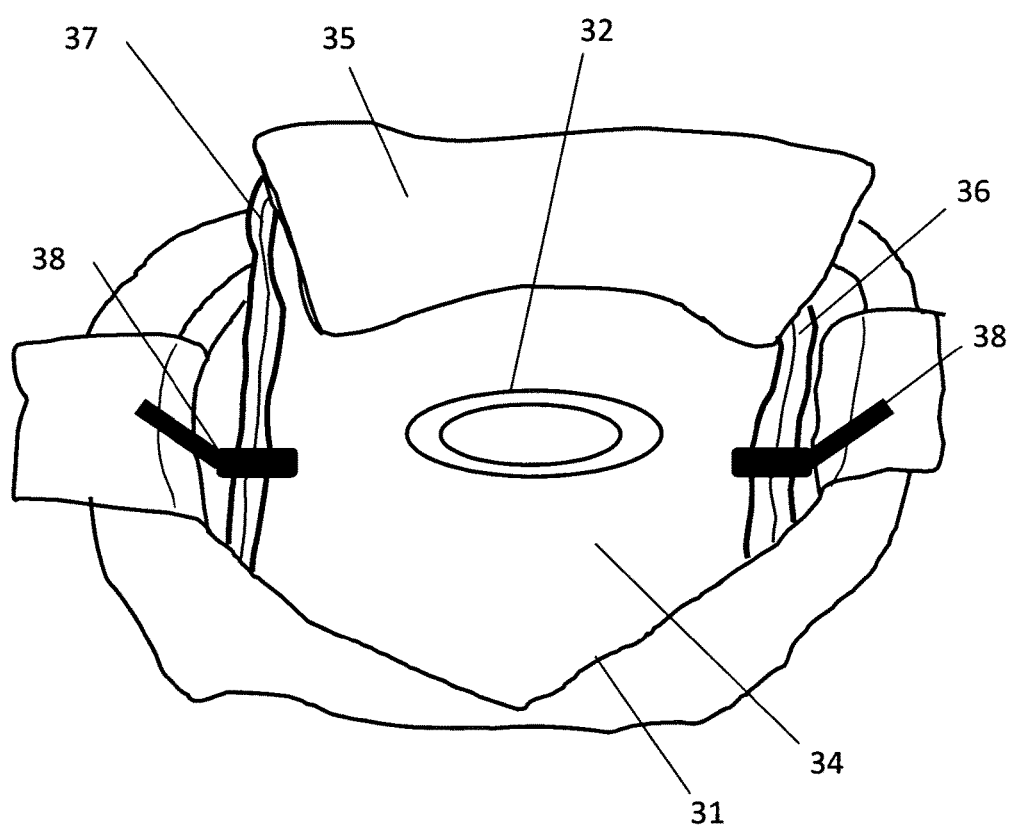
FIG. 5 is a top view of the incision after two atraumatic occlusion instruments are applied.

FIG. 4 and FIG. 5 show the places of the occlusion of the uterine vessels. The width of each of the sets of uterine blood vessels 36 and 37 can be up to 40 mm or even more. We prefer the following way to apply a clamp 38. Both, the artery and vein 37 are gently elevated by a surgeon hand, while the uterus is held by the other surgeon (an assistant). The Fallopian tubes are elevated, so they do not get clamped during vessel occlusion. The uterine clamp 38 is wide opened and the jaws 63 and 64 with cover 65 and 66, respectively, are positioned perpendicularly against the blood vessels 37. The posterior jaw of the clamp (jaw 64 with cover 66) is placed under the blood vessels 37 and anterior jaw of the clamp (jaw 63 with cover 65) is placed above of the blood vessels 37. After the proper placement is confirmed, the handles 54 and 55 of the clamp are closed and locked by engaging teeth 60 of the lugs 57 and 56. The surgeon controls the pressure applied to the vessels. The pressure is adjusted to at least partially or, mostly preferred; completely obstruct the vessels 37, so that the blood flow decreases and bleeding is minimized. Such pressure is atraumatic to the vessels, because the covers 65 and 66 cause obstruction of the vessels, but does not cause the damage. The occluded vessels 37 are shown on the FIG. 24-26. The procedure is repeated on the opposite side of the patient to occlude the blood vessels 36. The application of the both clamps can be done under one minute.

The optimal position of the clamp would be lower than the level of the uterine incision 32. Each occlusion instrument 38 is adjusted to be placed on the abdomen after the occlusion of the vessels is complete. The profile of the clamp fits the abdomen of the patient. State of the art instruments are not convenient for this purpose because they do not fit the profile of abdomen of the patient.

Figure 6:
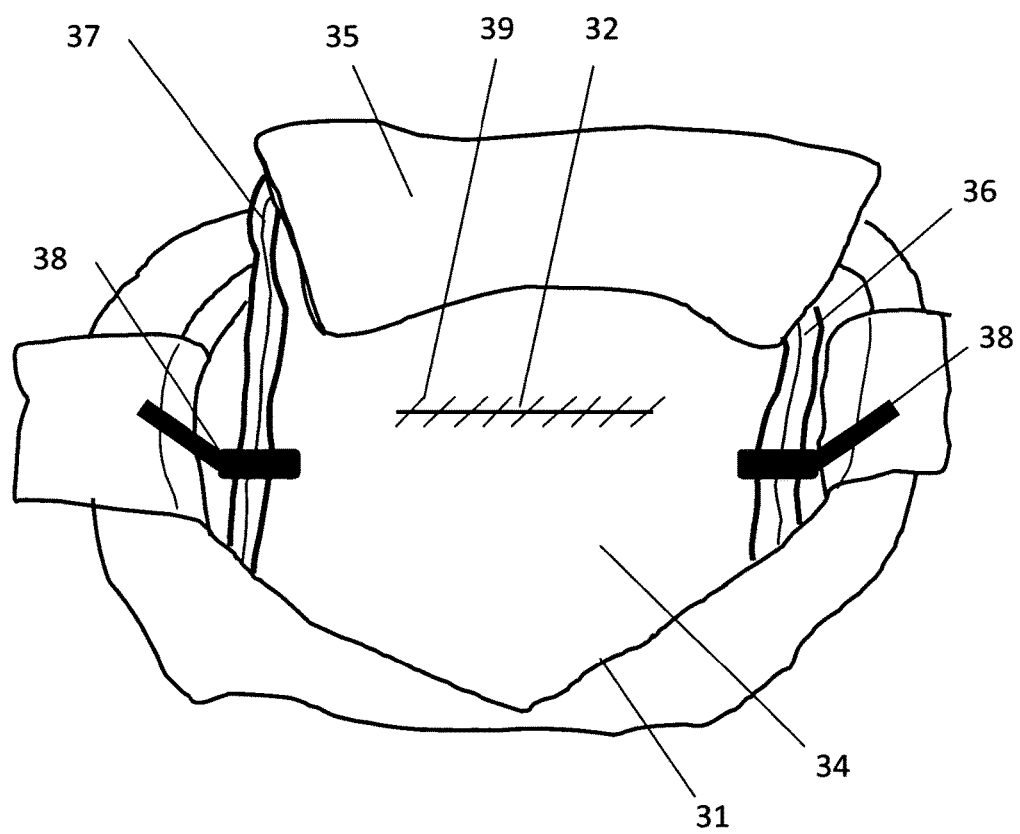
FIG. 6 is a top view of the incision after suturing of the uterus.

After occlusion of the uterine arteries, the bleeding of the incision 32 of the uterus 34 is significantly reduced or stopped. Stopping the bleeding eliminates or significantly reduces the need to clean the area of suturing and thus reduces the total time to close the uterus. Otherwise, suturing of the incision of the uterus is well known. FIG. 6 depicts the closed incision 32 by the suture 39. Stopping the bleeding of the incision 32 of the uterus and shortening the time of the suturing by non-invasive, non-permanent occlusion of the uterine blood vessels reduces blood loss by the patient which is the primary objective of the invention. Shortening the time toe suture of the incision 32 of the uterus reduces the surgery time.

Figure 7:
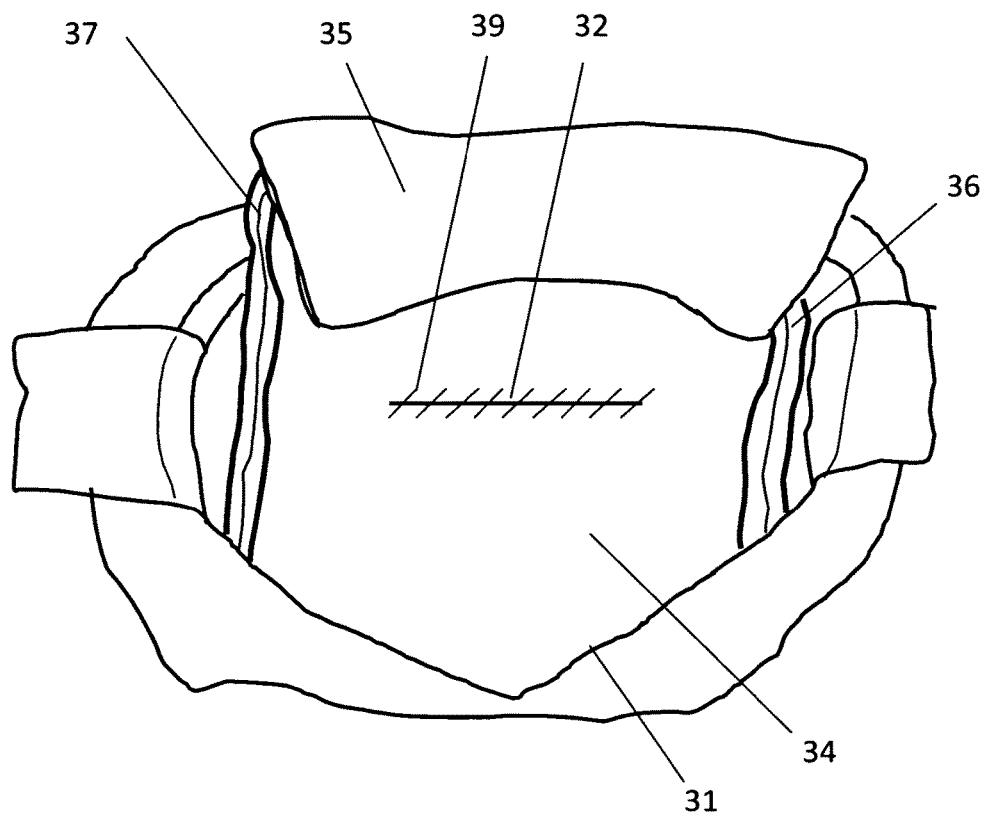
FIG. 7 is a top view of the incision after removal of occlusion instruments.
Figure 8:
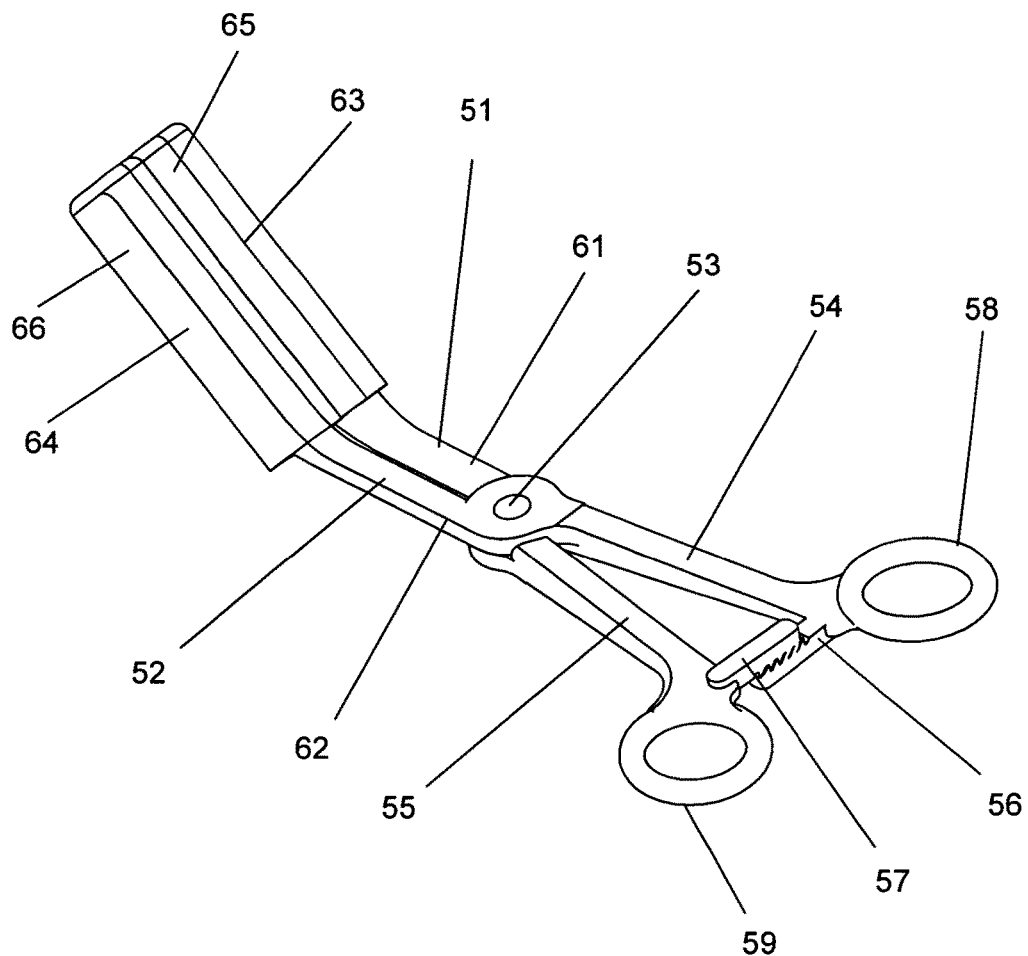
FIG. 8 is a perspective view of a clamp with closed jaws.
Figure 9:
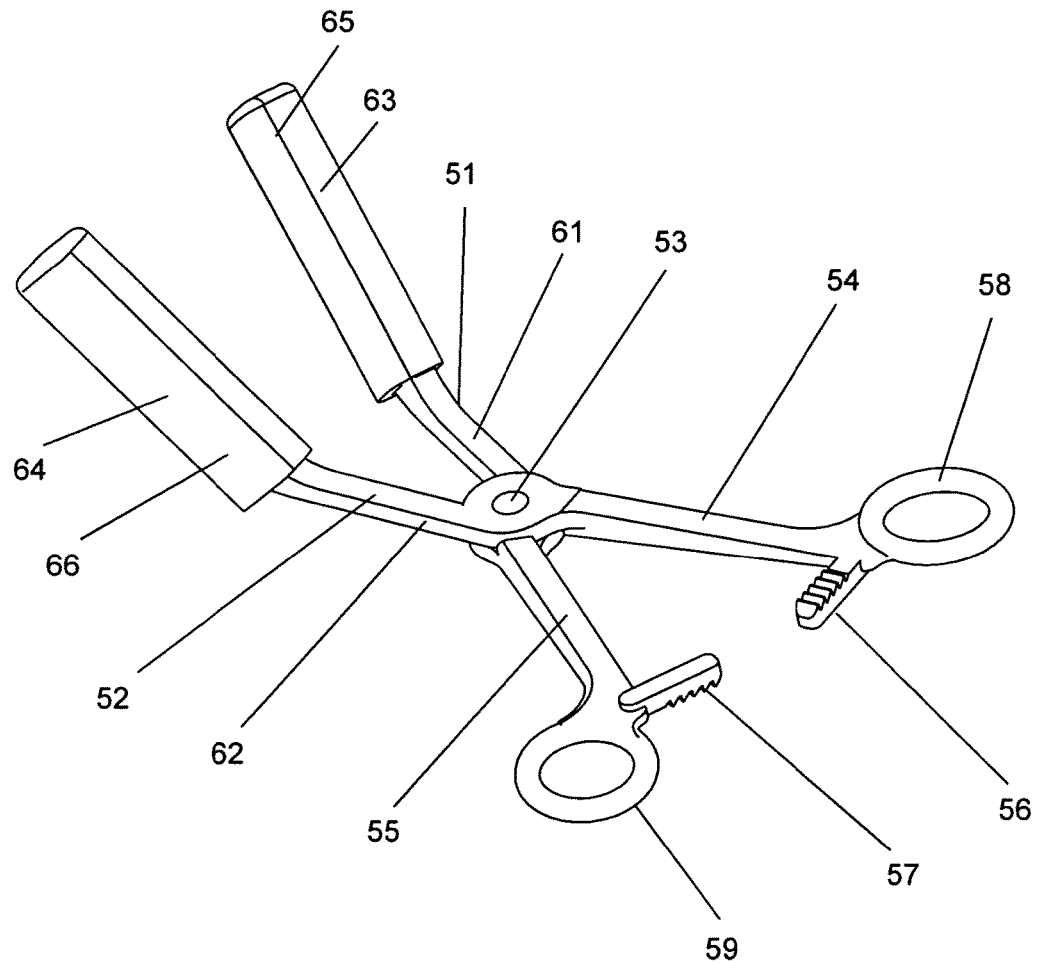
FIG. 9 is a perspective view of a clamp with open jaws.

After suturing of the incision 32 of the uterus, the occlusion instruments 38 are removed as shown on FIG. 7. The removal of the occlusion reestablishes the blood flow in the uterine vessels 36 and 37. The closure of the uterine vessels by the atraumatic occlusion instruments does not cause damage to the vessels, uterus or other problems. After removal of the occlusion instruments 38, the patient is closed in a well, traditional way.

The width of each set of a uterine artery and vein 36 and 37 can be up to 40 mm or even more. There is no atraumatic instrument for occlusion of so wide vessels. Even though we need to occlude arteries only, it is easier to occlude both the artery and the vein in each set of uterine blood vessels 36 and 37 because the artery and its vein are so closed and covered with a membrane.

The instrument 38 can be applied promptly, easily, and safely on the uterine arteries. It is applied to the both uterine sides on the uterine vessels. The pressure on the vessels decreases the blood flow to the uterus, or it stops it completely, for the period of time needed to close the uterine incision. It minimizes the blood loss and also allows easier closure of the incision and possible uterine laceration. When the uterus is closed and blood loss is not the problem anymore, the clamp can be easily removed.

A clamp 38, illustrated in FIGS. 8-11, has a pair of opposing jaws 51 and 52 which are pivotal relative to each other at a fulcrum 53 by the operation of associated scissor-type handles 54 and 55. The jaw 51 is integrated with the handle 54 and the jaw 52 is integrated with the handle 55 to provide the scissors action for opening and closing the jaws.

The handles 54 and 55 have the lugs 56 and 57 equipped with the interengaging ratchet teeth 60 to lock the jaws in closed or partially closed positions. The lugs 56 and 57 are provided in a distance from the hinge or pivot point 53 adjacent the point where the handles 54 and 55 terminate in the finger rings 58 and 59. The lugs 56 and 57 can be locked at different points to allow a surgeon to determine the amount of pressure applied to the uterine vessels.

Figure 11:
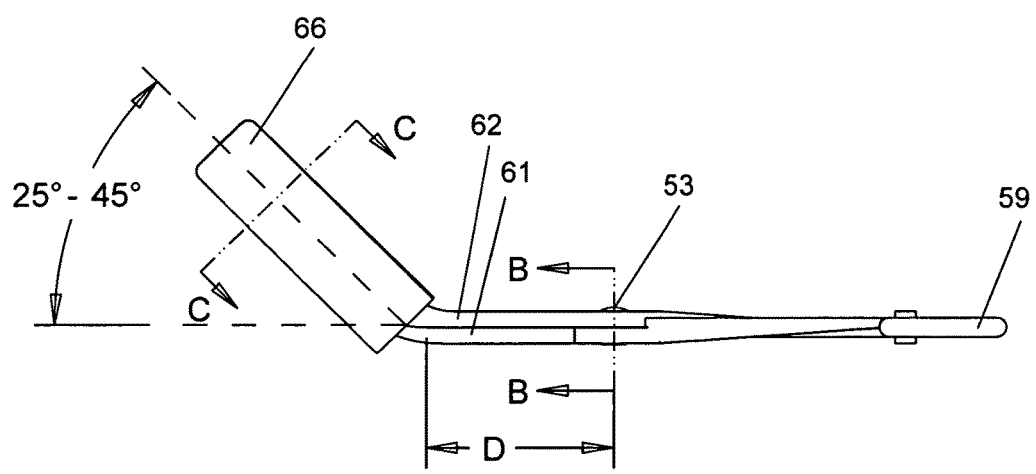
FIG. 11 is a side view of a clamp.
Figure 12:
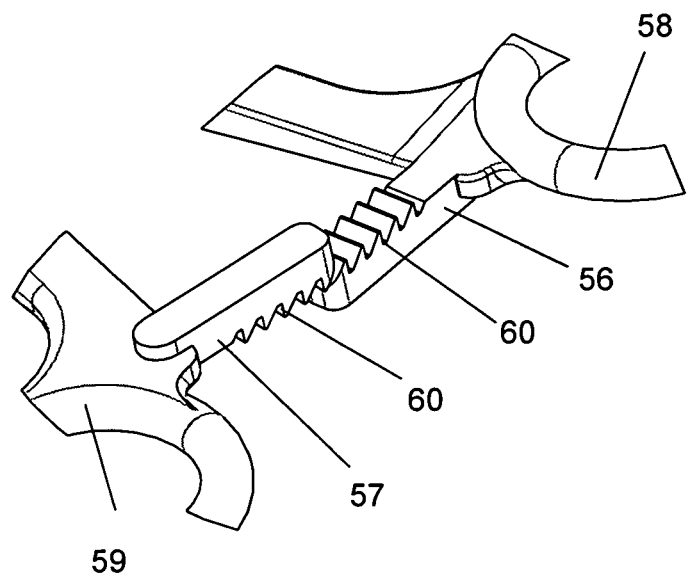
FIG. 12 is an enlarged perspective view of locking mechanism.
Figure 13:
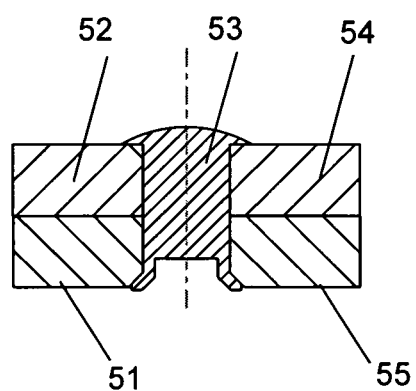
FIG. 13 is a cross section view taken along lines B-B of FIG. 10.

The clamp is adjusted to allow easier application on the uterine vessels and for placement of it on the patient abdomen while keeping the blood vessels occluded. The jaw 51 has the two straight members 61 and 63 connected with an angle 25-45 degrees. The preferred angle is 30-45 degrees. The jaw 52 has similar two straight members 62 and 64 connected with the same angle as the members 61 and 63. The angle shown on the FIG. 11 is 45 degrees. The preferred angle is needed to allow easier application on the uterine vessels. The preferable length D is 15-50 mm. The preferable length of the cover L is 50-60 mm. The preferred length of the clamp in its top view is 180-240 mm. The members 63 and 65 have the atraumatic covers or pads 65 and 66, respectively. We will use the term cover, although, a pad can be used instead of.

The handle jaw structures of reusable clamp can be made of metal and supplied with disposable covers or pads. The disposable pads require some time for attachment to the reusable clamps. A disposable clamp has handle jaw structures made of plastic and joined pivotally by a metal or plastic member 53. The disposable clamps are ready to use and do not take any additional time in the operating room to make the instruments ready for their application.

The jaws members 63 and 64 can have different shapes in their cross section, for example, they can be U-shaped, triangular, rectangular, square, rectangular tube, I-beam shaped, trapezoidal, etc.

Figure 10:
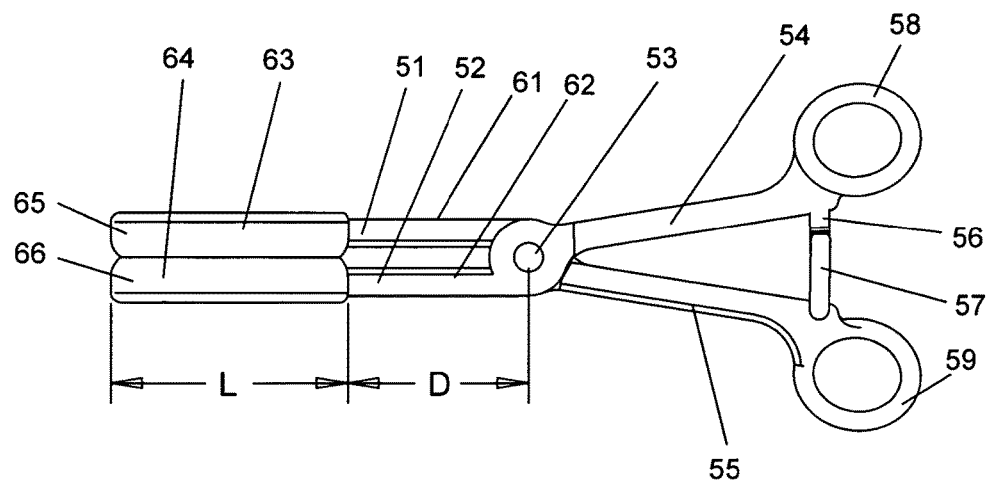
FIG. 10 is a top view of a clamp with closed jaws.
Figure 16:
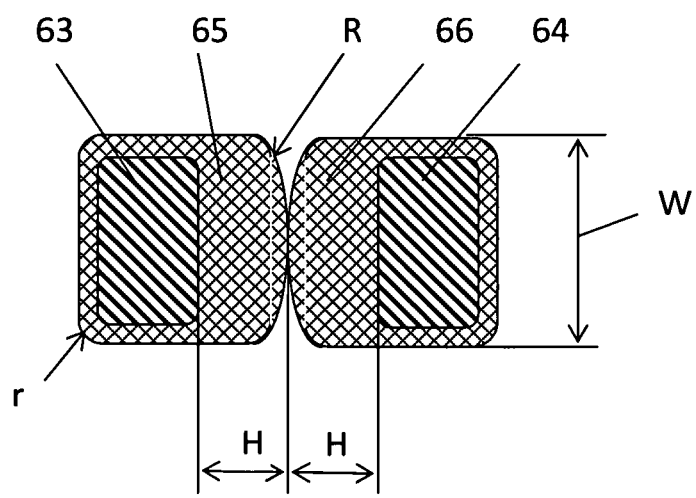
FIG. 16 is an enlarged cross section view taken along lines C-C of FIG. 10 depicting jaws with rectangular cross section.

FIG. 16 is an enlarged cross section view taken along lines C-C of FIG. 10 with rectangular jaw members 63 and 64. The working surface of the covers 65 and 66 can be flat as shown of FIG. 17 or have a radius R. The radius R can be much large than radius r. Radius r can be within 0.5-3 mm. The radius R can be 5-100 mm. The radius R can form the entire working surface of the covers as it is shown on the FIG. 16. The thickness H of the working side of the covers 65 and 66 is 3-15 mm. The preferred thickness is 5-10 mm. The width W of covers 65 and 66 is about 10 to 30 mm in order to prevent any damage to the uterine vessels.

Figure 17:
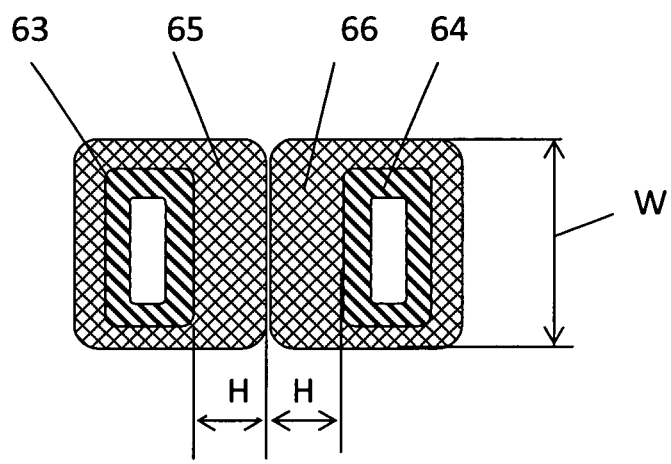
FIG. 17 is an enlarged cross section view taken along lines C-C of FIG. 10 depicting jaws with rectangular tubular cross section.

FIG. 17 is an enlarged cross section view taken along lines C-C of FIG. 10 depicting the jaw members 63 and 64 with rectangular tubular cross section. The working surface of the covers 65 and 66 is shown flat.

Figure 18:
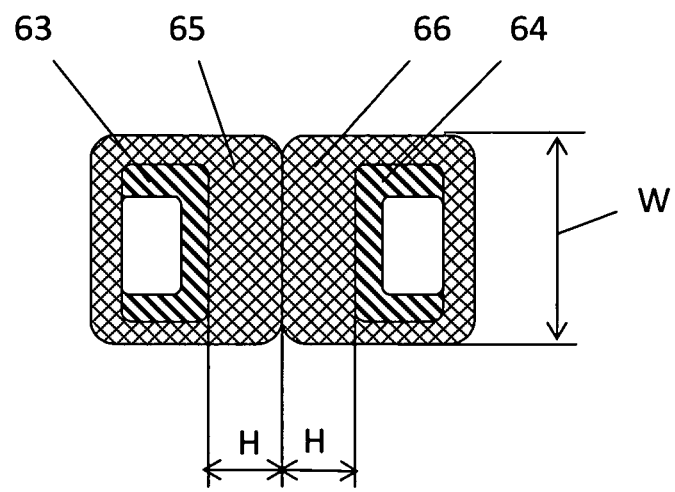
FIG. 18 is an enlarged cross section view taken along lines C-C of FIG. 10 depicting jaws with U-shaped cross section.

FIG. 18 is an enlarged cross section view taken along lines C-C of FIG. 10 depicting the jaw members 63 and 64 with U-shaped cross section. The working surface of the covers 65 and 66 is shown flat.

Figure 14:
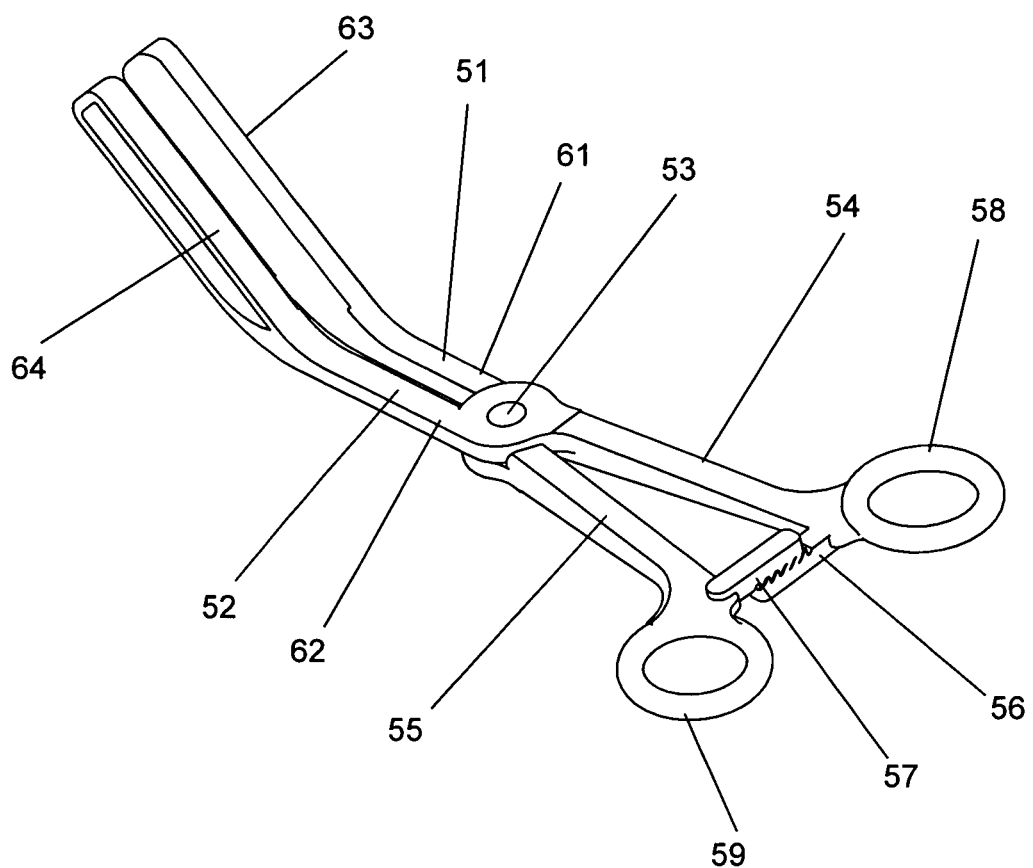
FIG. 14 is a perspective view of a clamp with closed u-shaped jaws without covers.
Figure 15:
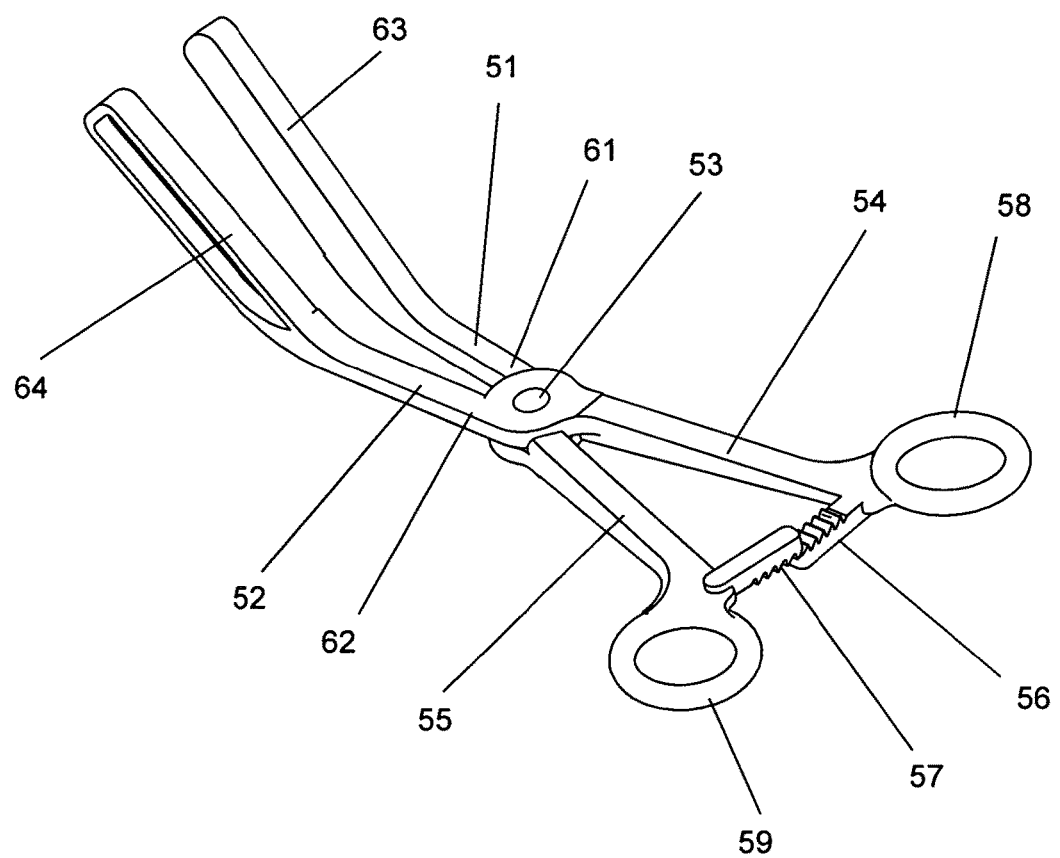
FIG. 15 is a perspective view of a clamp with open u-shaped jaws without covers.

The perspective view of the clamp depicting U-shaped jaw members 63 and 64 without covers shown on FIG. 14 and FIG. 15.

Figure 19:
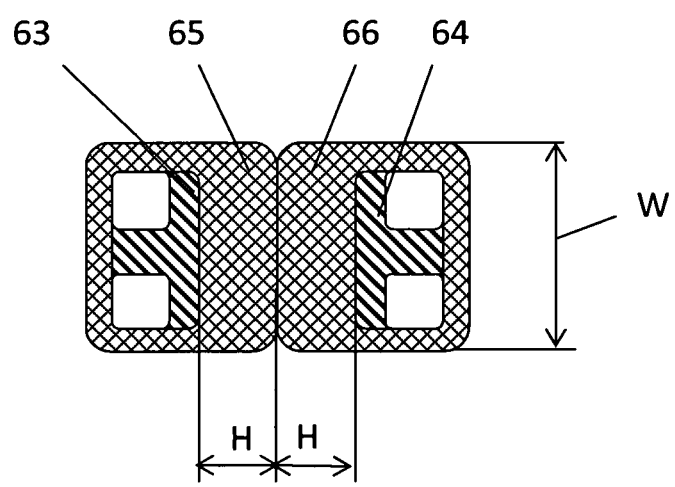
FIG. 19 is an enlarged cross section view taken along lines C-C of FIG. 10 depicting jaws with T-shaped cross section.

FIG. 19 is an enlarged cross section view taken along lines C-C of FIG. 10 depicting jaw members 63 and 64 with T-shaped cross section.

Figure 20:
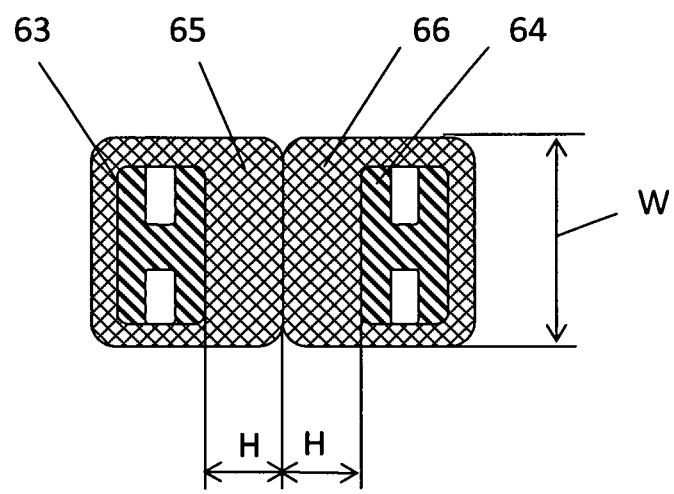
FIG. 20 is an enlarged cross section view taken along lines C-C of FIG. 10 depicting jaws with I-beam cross section.

FIG. 20 is an enlarged cross section view taken along lines C-C of FIG. 10 depicting jaw members 63 and 64 with I-beam cross section.

Figure 21:
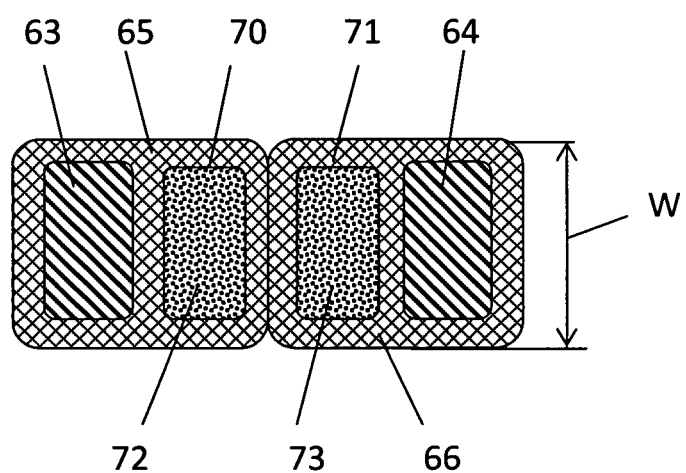
FIG. 21 is an enlarged cross section view taken along lines C-C of FIG. 10 depicting double-tubular covers.

FIG. 21 is an enlarged cross section view taken along lines C-C of FIG. 10 depicting the double-tubular covers 65 and 66. Each cover 65 and 66 has a hole for inserting the jaws members 63 and 64, respectively. Each cover has an additional hole 70 and 71. The additional holes can be the same as the hole for inserting jaw member or have different shape and/or size in their cross section. The shape cross section of additional holes can be, for example, rectangular, square, oval, etc. The soft or resilient material 72 and 73 can be inserted in additional holes. It can be silicon, soft plastic, gauze, etc.

Figure 22:
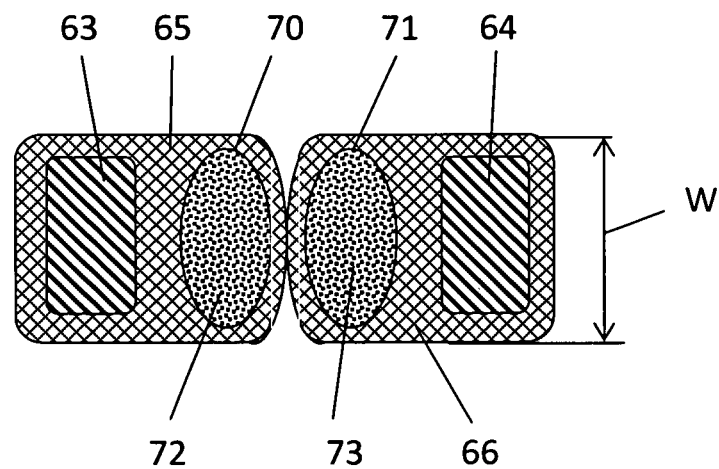
FIG. 22 is an enlarged cross section view taken along lines C-C of FIG. 10 depicting double-tubular covers with oval cross section of the additional holes.
Figure 23:
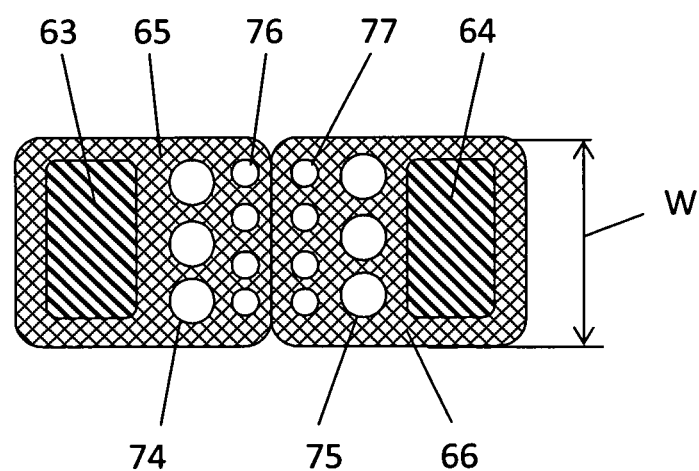
FIG. 23 is an enlarged cross section view taken along lines C-C of FIG. 10 depicting covers with plurality additional holes.

FIG. 22 is an enlarged cross section view taken along lines C-C of FIG. 10 depicting the double-tubular covers 65 and 66 with oval cross section of the additional holes. FIG. 23 is an enlarged cross section view taken along lines C-C of FIG. 10 depicting the covers 65 and 66 with plurality additional holes 74, 76, 77 and 75. The holes can have different shape and/or size in their cross sections. The holes can be empty or at least some of them can have inserts.

Figure 24:
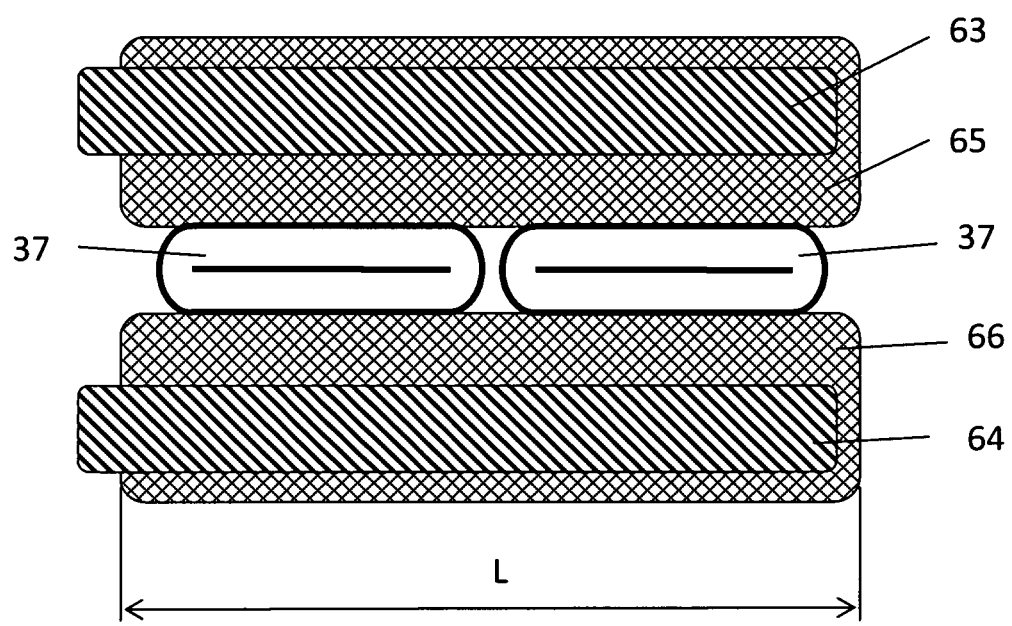
FIG. 24 is an enlarged cross section view taken along lines A-A of FIG. 4 showing occluded uterine blood vessels.

FIG. 24 is an enlarged cross section view taken along lines A-A of FIG. 4 showing the occluded uterine blood vessels 37. The length L of the covers 65 and 66 has to be long enough to cover the entire width of uterine vessels which is about at 40 mm or more when they are exposed after placing the uterine round ligament 37 on the abdomen. As a result, the preferred length of covers 65 and 66 is about 45 mm to 75 mm to cover the entire width of the uterine vessels. The preferred length L is 50-60 mm.

Figure 25:
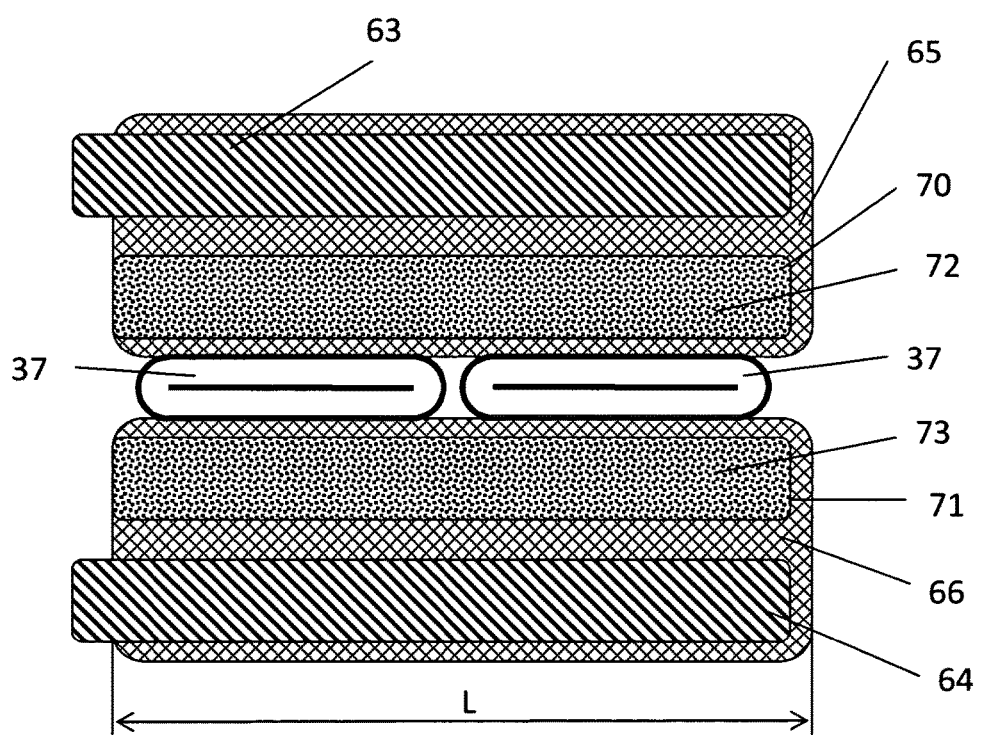
FIG. 25 is an enlarged cross section view taken along lines A-A of FIG. 4 showing occluded uterine blood vessels using a clamp with double tubular covers.

FIG. 25 is an enlarged cross section view taken along lines A-A of FIG. 4 showing the occluded uterine blood vessels 35 using a clamp with double tubular covers 65 and 66. The additional holes 70 and 71 in the covers 65 and 66 are filled with inserts 72 and 73.

Figure 26:
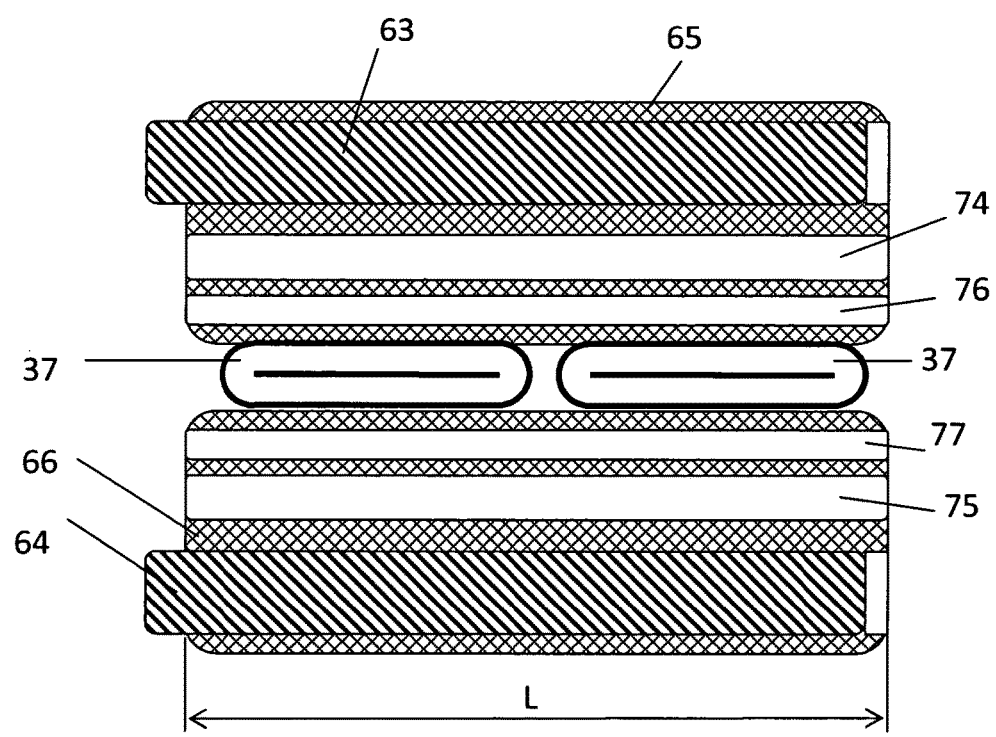
FIG. 26 is an enlarged cross section view taken along lines A-A of FIG. 4 showing occluded uterine blood vessels using a clamp with having empty additional holes.

FIG. 26 is an enlarged cross section view taken along lines A-A of FIG. 4 showing the occluded uterine blood vessels 37 using a clamp with covers 65 and 66 having additional empty holes 74-76.

The covers 65 and 66 can have holes with both ends open as shown on the FIG. 26 or with one end closed as shown in the FIGS. 24 and 25. The covers with one end closed can be molded.

The covers 65 and 66 can be tubular as they shown on the FIG. 26. They can be molded or extruded. Covers can be overmolded. Covers can be made of silicon, rubber-like materials, soft plastic, foam, resilient material, etc. The tubular covers can be made of gauzes or fabric. The tubular covers can be woven.

Figure 27:
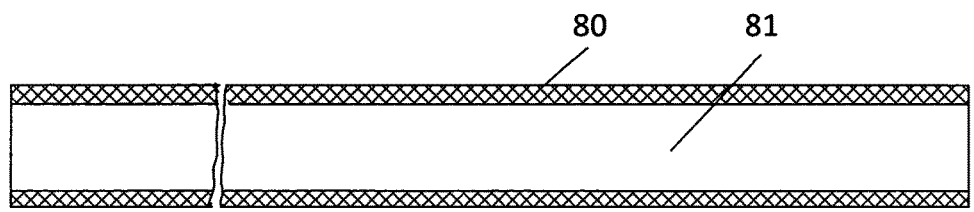
FIG. 27 is a cross section of a work piece of a cover.

FIG. 27 is a cross section of a work piece (preferably, made of fabric, but not limited) of a cover 65 (or 66). The tube 80 has a whole 81.

Figure 28:
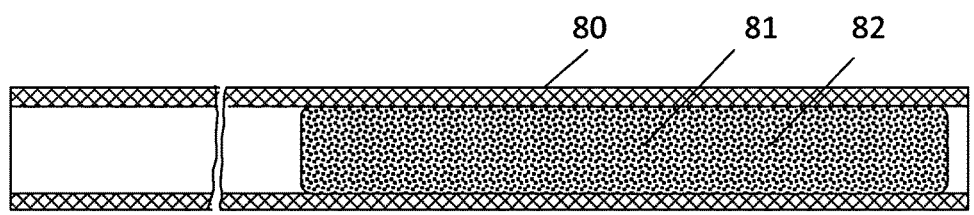
FIG. 28 depicts the work piece of a cover with an insert placed into its hole.

FIG. 28 depicts the work piece of a cover with an insert 72 (or 73) inserted into the hole.

Figure 29:
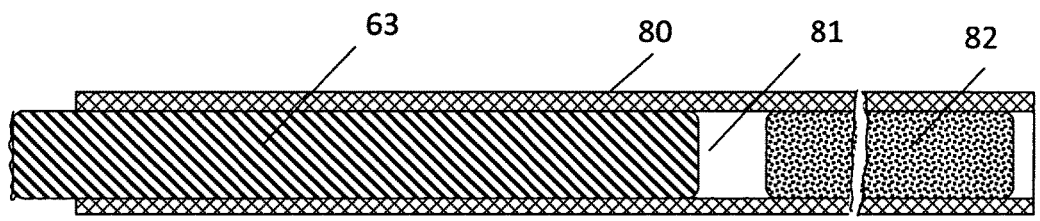
FIG. 29 depicts the work piece of a cover with a jaw member inserted into the hole.

FIG. 29 depicts the work piece of a cover with jaw member 63 (or 64) inserted into the hole 81. A gap between the insert and the jaw member depends on the thickness of jaw member.

Figure 30:
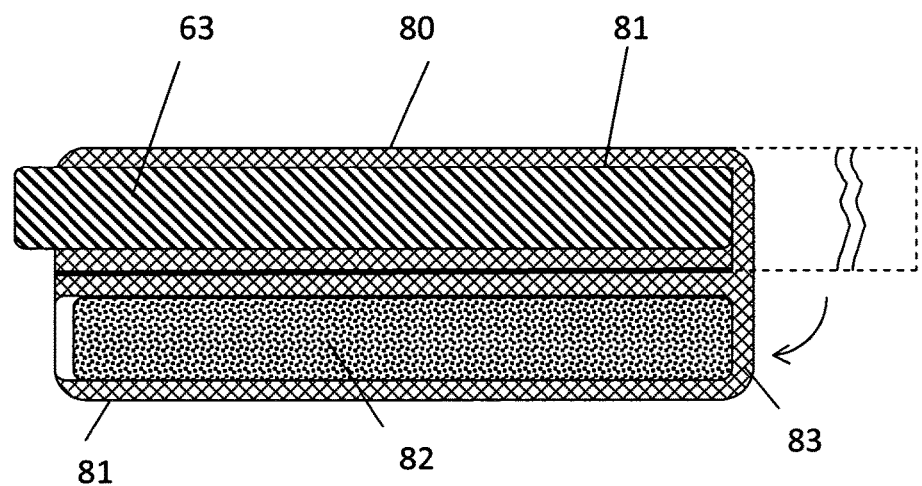
FIG. 30 depicts the work piece bent into a cover.

FIG. 30 depicts the work piece bent into a cover 65 (or 66). Bent sections of the work piece are connected together. The closed end covers can be made by folding a tubular work piece and attaching the folded parts together by sewing, using adhesive or double-sided adhesive tape. Also, an intermediate plastic film can be inserted between folded parts along surface 83 and melted to hold folded parts together. Folded plastic material can be welded together at least in several points. Folded fabric cover parts can be connected by sewing them together. The covers can be folded and their bent parts connected together before they are assembled with the clamps. The covers can be folded and their bent parts connected together after jaw members are inserted into the corresponding holes.

Figure 31:
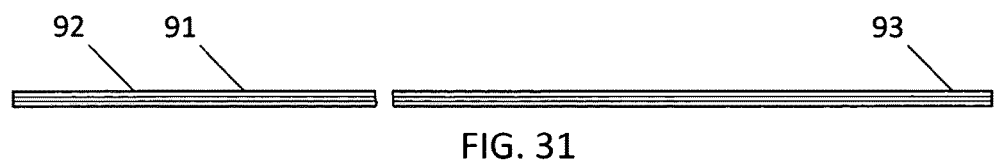
FIG. 31 depicts a gauze or fabric work piece of a cover.

FIG. 31 depicts a gauze or fabric work piece 91 of a cover. The work piece 91 has all side edges folded inside (not shown) as it is known in the art surgical sponges. The work piece 91 has the ends 92 and 93. Providing the work piece 91 is the first step in making the cover according to one of embodiments.

Figure 32:
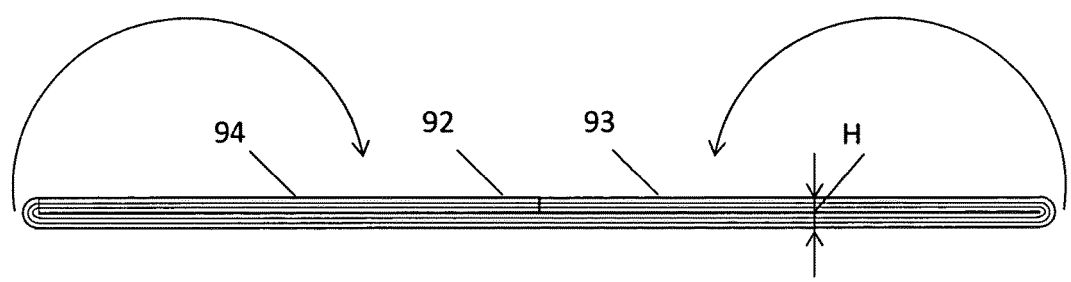
FIG. 32 depicts the second step in making the cover out of work piece shown on the FIG. 31.

FIG. 32 depicts the second step in making the cover out of work piece shown on the FIG. 31. The ends 92 and 93 are bent and folded so they meet each other at the center of created part 94 or in a close proximity from each other. The folding ends 92 and 93 provides the part 94 with rounded ends and with no edges of the layers of the gauze. The part 94 is twice thicker than work piece 91. The thickness H of the part 94 can be 3-15 mm, preferably, 5-10 mm. The part 94 can be made of 16-50 layers of gauze, preferably 24-40 layers.

Figure 33:
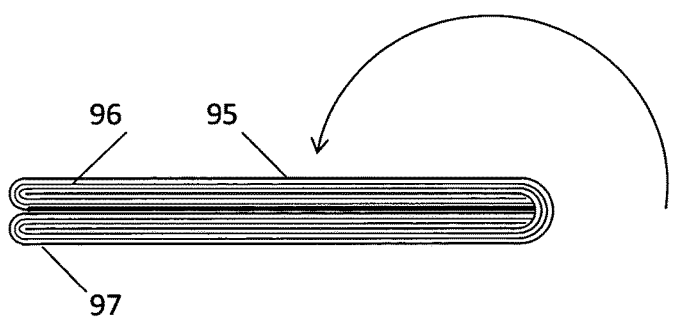
FIG. 33 depicts the third step in making the cover out of gauze of fabric work piece shown on the FIG. 31.

FIG. 33 depicts the third step in making the cover out of gauze of fabric work piece shown on the FIG. 31. Tart 94 is folded symmetrically creating a part 95 comprising members 96 and 97 and a rounded end connecting these two members. All original edges of any single piece of fabric or gauze used in part 95 have to be folded inside the part. Any of its sides has to have no original edges.

Figure 34:
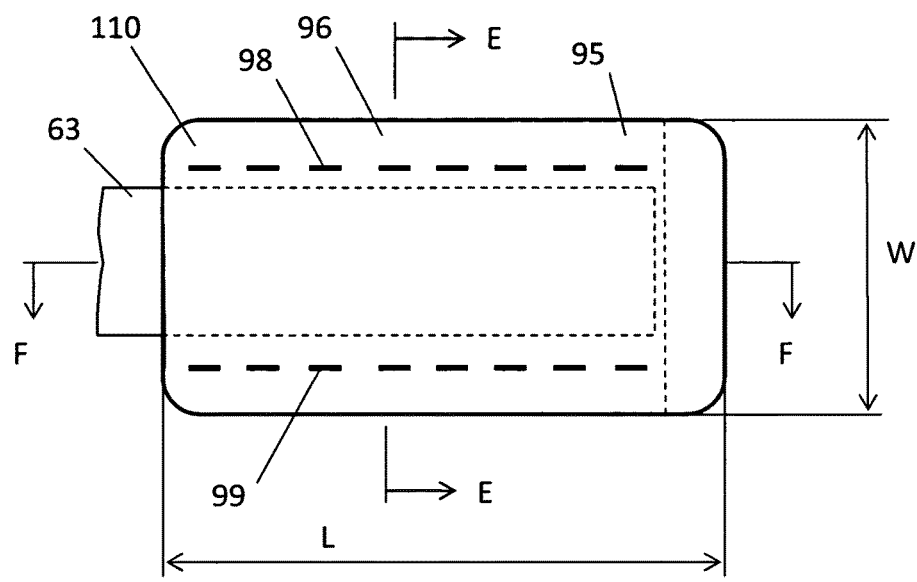
FIG. 34 is an enlarged top view of a cover on a jaw of the instrument.

FIG. 34 is an enlarged top view of a cover on a jaw of the instrument. The fourth step in making the cover is connecting the members 96 and 97 along both of its long sides, for example by sewing them together. The seam 98 and seam 99 not only connect members 96 and 97, but also create a space between the seams for inserting a member of a jaw. The sewing members 96 and 97 create the cover 110.

FIG. 34 shows the member 63 of the jaw inserted into the space between the seams 98 and 99 until the end of the space between members 96 and 97. The cross section of the space is made smaller than the cross section of the member of a jaw. Inserting the member of the jaw stretches the cover 110 securing the cover in its position due to elasticity of the cover 110. The preferred length L of the cover 110 is 50-60 mm. The width W of the covers is about 10 to 30 mm in order to prevent any damage to the uterine vessels. The preferred width W of the cover 110 is 12-25 mm.

Figure 35:
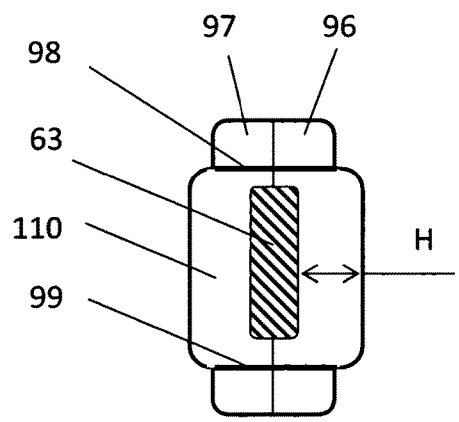
FIG. 35 is an enlarged cross section view taken along lines E-E of FIG. 34.
Figure 36:
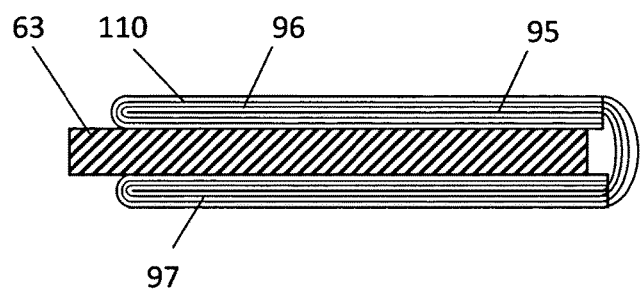
FIG. 36 is an enlarged cross section view taken along lines F-F of FIG. 34.

FIG. 35 is an enlarged cross section view taken along lines E-E of FIG. 34. FIG. 36 is an enlarged cross section view taken along lines F-F of FIG. 34.

Figure 37:
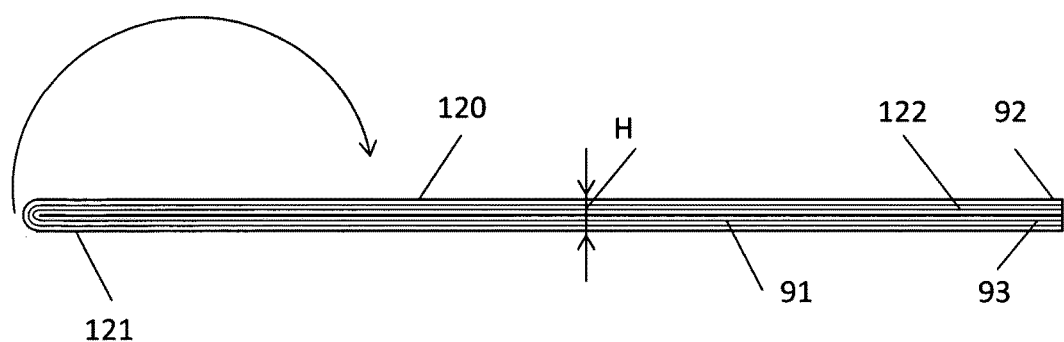
FIG. 37 depicts another gauze or fabric work piece of a cover.

FIG. 37 depicts gauze or fabric work piece 120 of a cover. This is the second step in making the cover out of work piece 91 shown on the FIG. 31. Folding the ends 92 and 93 and bringing them together provides the part 120 with rounded end 121. The ends 92 and 93 are placed at the end 122 of the part 120. The part 120 is twice thicker than the work piece 91. The thickness H of the part 120 can be 3-15 mm, preferably, 5-10 mm.

The part 120 can be made of 16-50 layers of gauze, preferably 24-40.

Figure 38:
FIG. 38 is an enlarged top view of part 120 after sewing ends 92 and 93.

FIG. 38 is an enlarged top view of the part 120 after sewing ends 92 and 93 at the end 122 with seam 123. Bonding the ends 92 and 93 simplifies the insertion of the member of the jaw and eliminates possibility of inserting the member of the jaw between wrong layers of the gauze.

Figure 39:
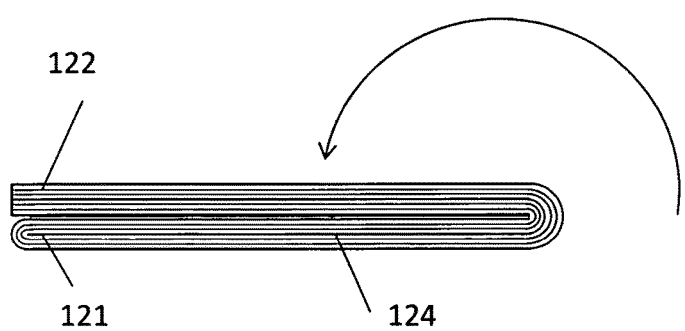
FIG. 39 depicts folding the work piece 120.

FIG. 39 depicts folding the work piece 120 symmetrically while creating a part 124 comprising the members with ends 122 and 123 and a rounded end connecting these two members. All original edges of any single piece of fabric or gauze used in part 124 has to be folded inside the part. Any of its sides has to have no original edges.

Figure 40:
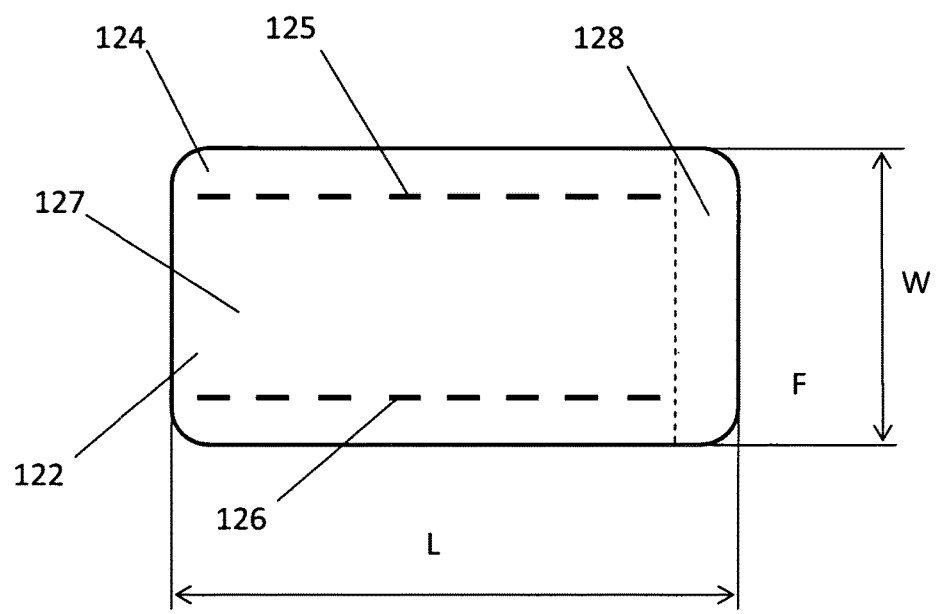
FIG. 40 is an enlarged top view of a cover on a jaw of the instrument.

FIG. 40 is an enlarged top view of a cover on a jaw of the instrument. The members with ends 122 and 123 are connected along both of its long sides, for example by sewing them together. The seams 125 and 126 not only connect the members 122 and 123, but also create a space 127 between the seams for inserting a member of a jaw. The sewing members 122 and 123 create the cover 128. All original edges of any single piece of fabric or gauze used in the cover 128 have to be folded inside the part. Any of its sides has to have no original edges.

Figure 41:
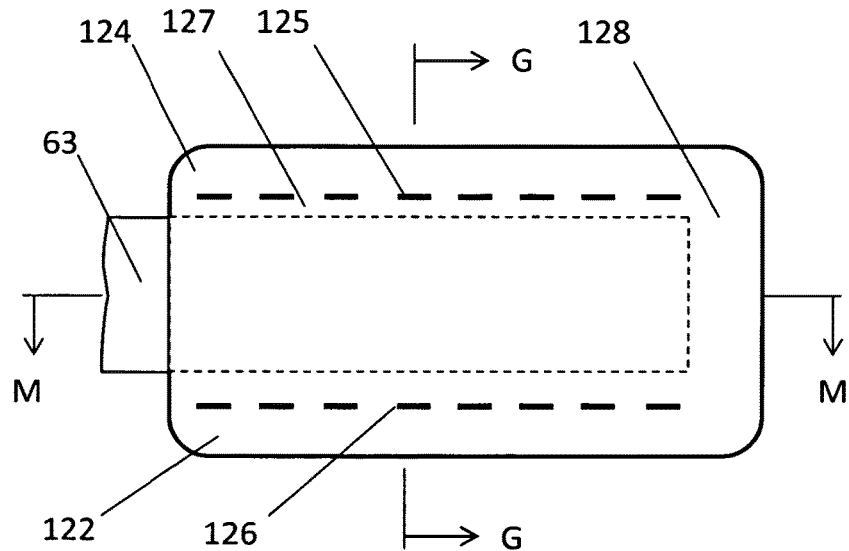
FIG. 41 is an enlarged top view of a cover on a jaw of the instrument.

FIG. 41 is an enlarged top view of a cover 128 on a jaw of the instrument.

Figure 42:
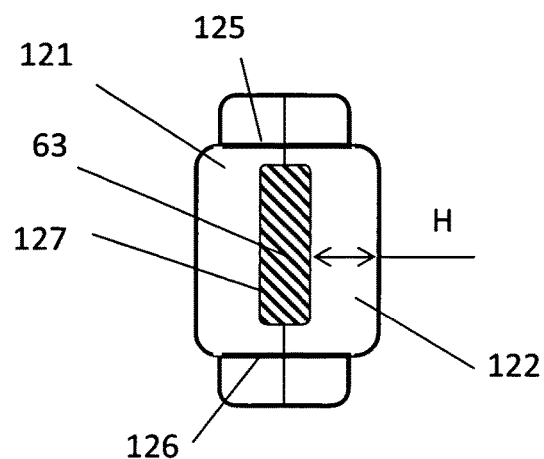
FIG. 42 is an enlarged cross section view taken along lines G-G of FIG. 41.
Figure 43:
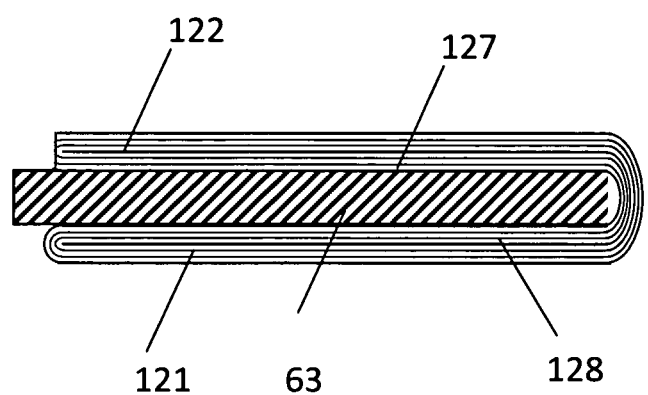
FIG. 43 is an enlarged cross section view taken along lines M-M of FIG. 41.

FIG. 42 is an enlarged cross section view taken along lines G-G of FIG. 41. FIG. 43 is an enlarged cross section view taken along lines M-M of FIG. 41. The member 63 of a jaw is inserted into the space 127 between the seams 125 and 126 until the end of the space between members 122 and 123. The cross section of the space is made less than the cross section of the member of a jaw. Inserting the member of the jaw stretches the cover 128 securing it in its position due to elasticity of the cover 128.

The preferred length L of the cover 128 is 50-60 mm. The width W of the covers is about 10 to 30 mm in order to prevent any damage to the uterine vessels. The preferred width W of the cover 128 is 12-25 mm.

Figure 44:
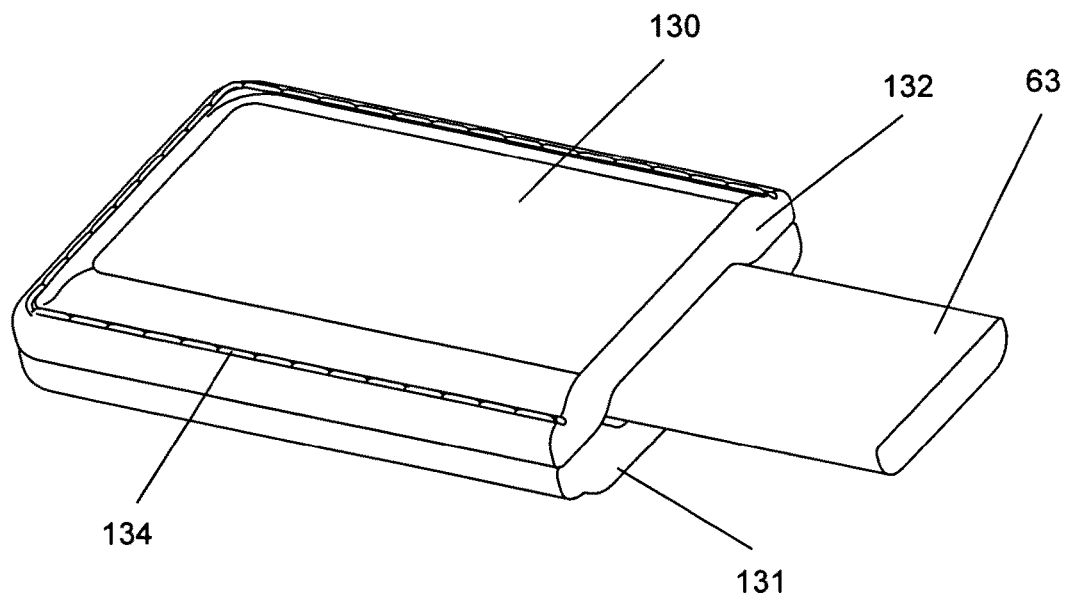
FIG. 44 is a perspective view of a cover 130 on a jaw of the instrument.
Figure 45:
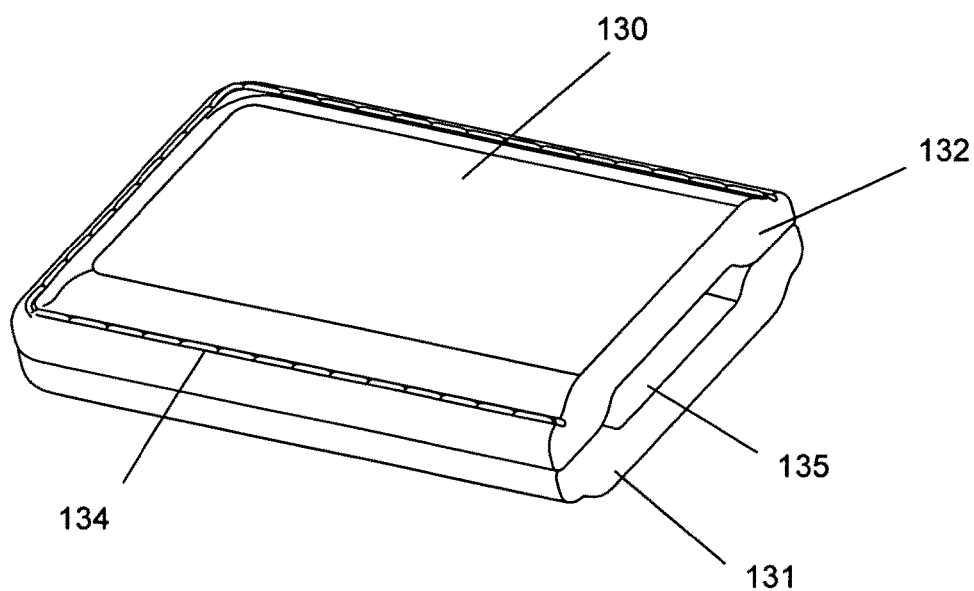
FIG. 45 is a perspective view of a cover 130.

FIG. 44 is a perspective view of a cover 130 on a jaw of the instrument. FIG. 45 is a perspective view of a cover 130. Cover 130 is made of two parts 131 and 132 sewed together with a seam 134. The seam 134 defines the space 135 for insertion of the member 63 of the jaw of an instrument.

Figure 46:
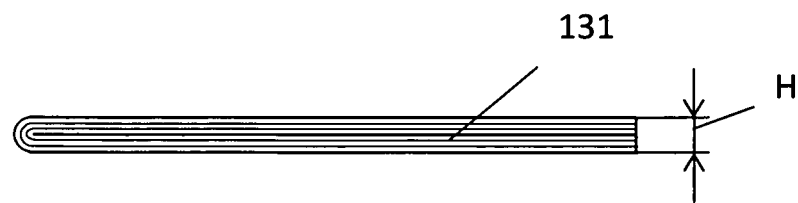
FIG. 46 depicts gauze or fabric work piece 131 of a cover 130.

FIGS. 46-49 explain the process of making the cover 130. FIG. 46 depicts one of two gauze or fabric work pieces of a cover 130. The thickness H of the work piece 131 can be 3-15 mm, preferably, 5-10 mm. The work piece 131 can be made of 16-50 layers of gauze, preferably, 24-40 layers. All original edges of any single piece of fabric or gauze used in part 131 and 132 have to be folded inside the part. Any of its sides has to have no original edges. The part 132 will be placed on a working side of the cover 130 to be engaged with blood vessels.

Figure 47:
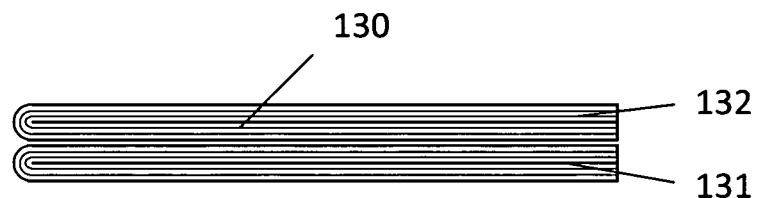
FIG. 47 is a side view of the cover 130.
Figure 48:
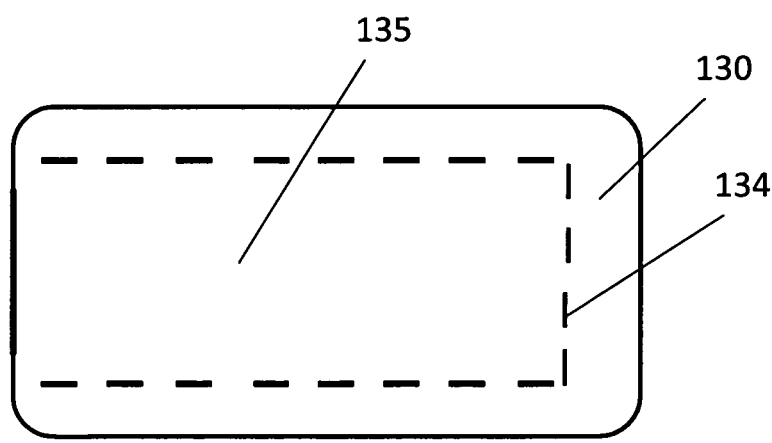
FIG. 48 is an enlarged top view of a cover 130.

The FIG. 47 is a side view of the cover 130 comprising two parts 131 and 132. The part 132 can be identical to the part 131 or can be made thinner. FIG. 48 is an enlarged top view of a cover 130. The parts 131 and 132 are connected along both of its long sides, for example, by sewing them together. The seam 134 defines a space 135 for inserting and retaining a member of a jaw.

Figure 49:
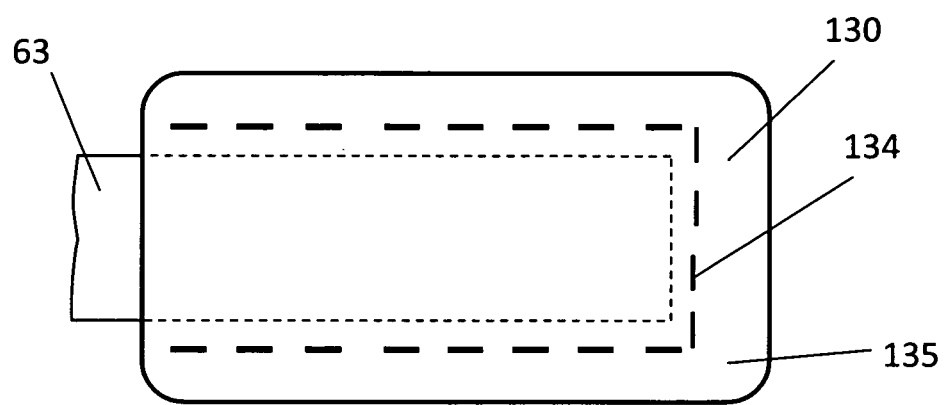
FIG. 49 is an enlarged top view of a cover 130 on a jaw of the instrument.

FIG. 49 is an enlarged top view of a cover 130 on a member 63 of a jaw of the instrument. The member 63 of a jaw is inserted into the space 135 defined by seam 135. The cross section of the space is made less than the cross section of the member of a jaw. Inserting the member of the jaw stretches the cover 130 securing the cover in its position due to elasticity of the cover 130.

The seam defines the thickness of the top and the sides of the cover. The preferable thickness of the sides and the top is 3-8 mm. The preferred length L of the cover 128 is 50-60 mm. The width W of the covers is about 10 to 30 mm in order to prevent any damage to the uterine vessels. The preferred width of the cover 128 is 12-25 mm.

Figure 50:
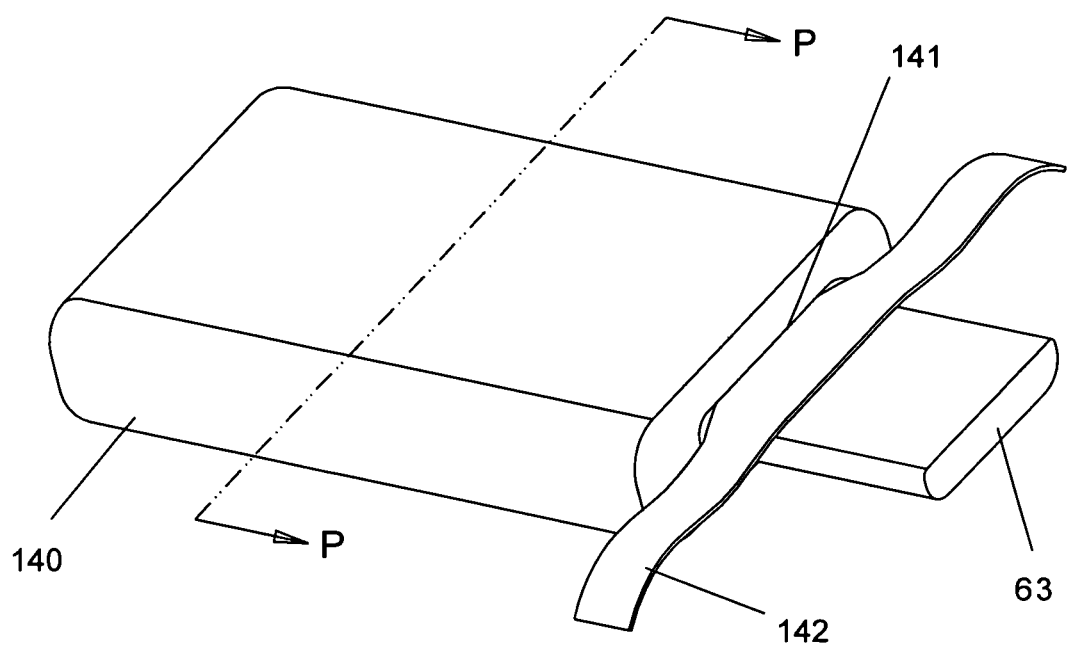
FIG. 50 is a perspective view of a cover 140 on a jaw of the instrument.
Figure 51:
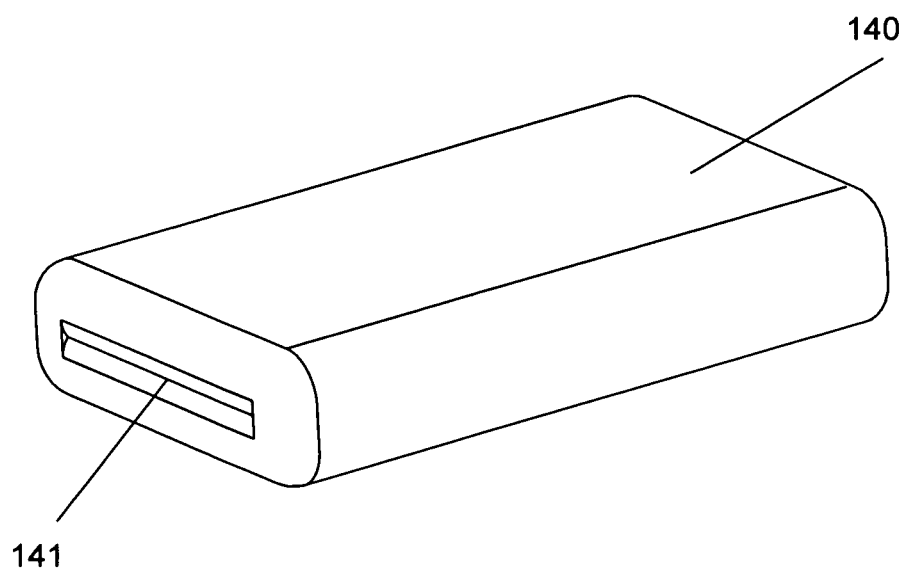
FIG. 51 is a perspective view of a cover 140.

FIG. 50 is a perspective view of a cover 140 on a jaw of the instrument. FIG. 51 is a perspective view of a cover 140. The cover 140 has a space 141 used for insertion of the member 63 of the jaw of an instrument. Any cover can be supplied with a lace 142.

Figure 52:
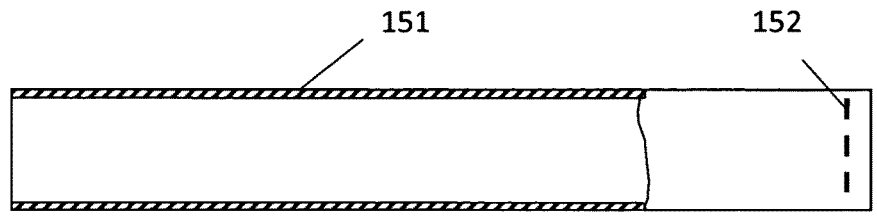
FIG. 52 depicts a tubular gauze.
Figure 53:
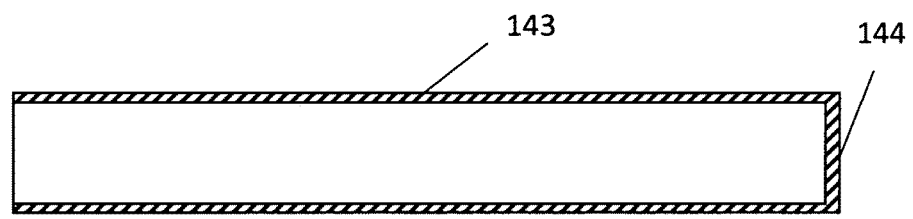
FIG. 53 depicts a tubular bag.
Figure 54:
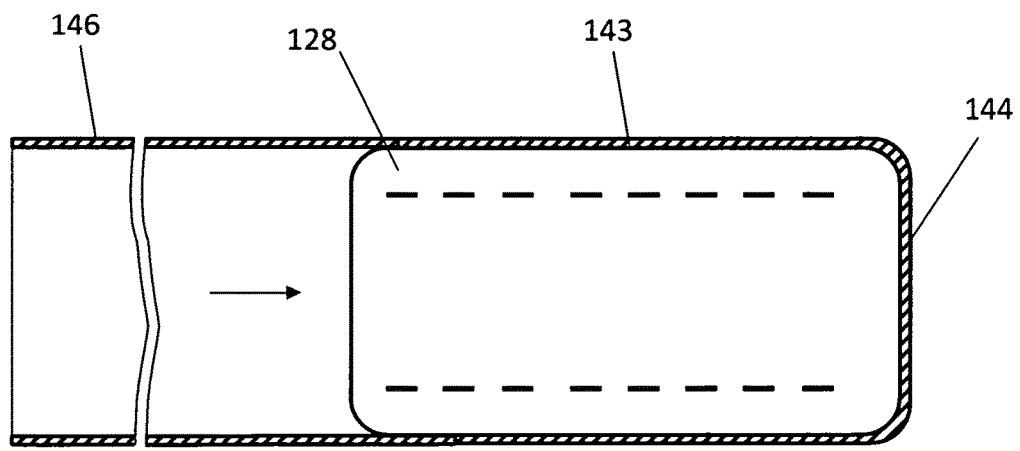
FIG. 54 shows insertion of an internal part of the cover inside the tubular bag 143.

FIGS. 52-60 explain the design and the process of making the cover 140. FIG. 52 depicts tubular gauze 151. It is provided with the seam 152. Preferably, the tubular gauze is turned inside out before receiving the seam 152. FIG. 53 depicts a tubular bag 143 obtained after turning the tubular gauze 151 inside out after receiving the seam 152 to keep the edge of the tubular gauze and the seam 152 inside. As a result, one end of the tubular bag 143 is closed by the wall 144. FIG. 54 shows an insertion of an internal part of the cover inside the tubular bag 143 until the internal part reaches the wall 144. FIG. 54 depicts the cover 128 inserted inside the bag 143. The length of the tubular bag exceeds the length of the insert 128 by the length of the part 146.

Figure 55:
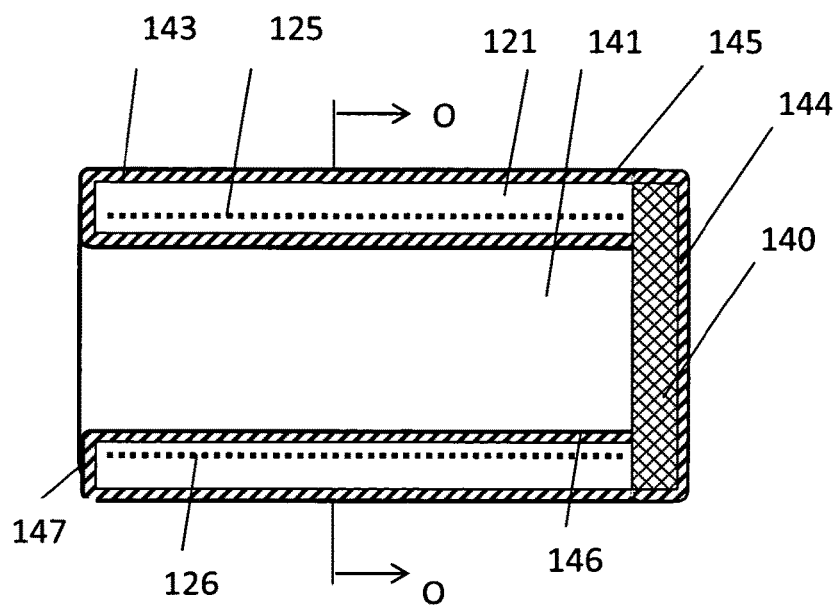
FIG. 55 is an enlarged cross section view taken along lines N-N of FIG. 51.

FIG. 55 is an enlarged cross section view taken along lines N-N of FIG. 51. FIG. 55 shows how the extended part 146 of the tubular bag 143 inserted inside the cover 128 between the members 121 and 122 connected by the seams 125 and 126. It is shown that the part 146 is inserted until it reaches the end of the internal cavity of the insert 128. However, the part 146 can be shorter. The insert 128 is completely covered outside by the tubular gauze parts 144, 145, 146 and 147. The cavity 141 is adapted to receive a member of a jaw of the instrument. The seams 125 and 126 define the thickness of the side walls of the cover 140 when the member of a jaw of the instrument is inserted.

Figures 56, 57:
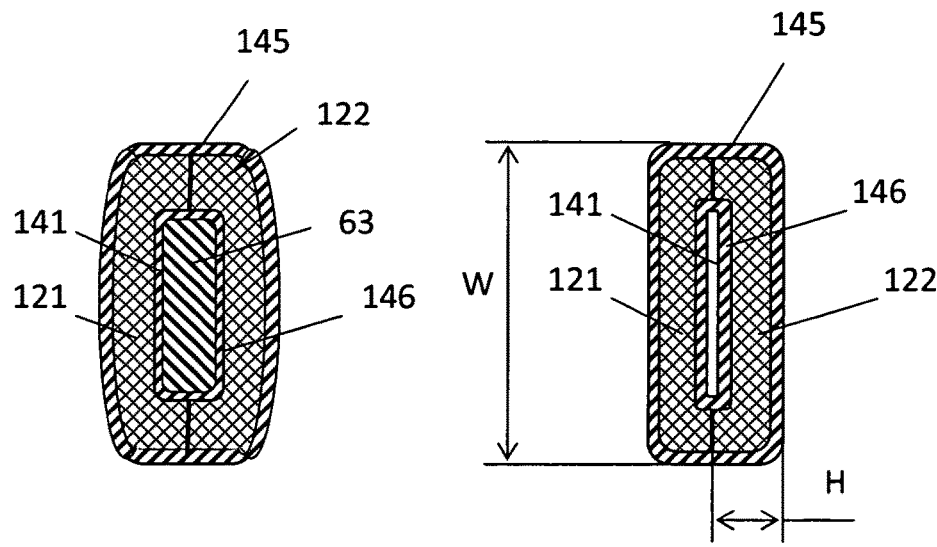
FIG. 56 is an enlarged cross section view taken along lines P-P of FIG. 50.
FIG. 57 is an enlarged cross section view taken along lines O-O of FIG. 55.
Figure 58:
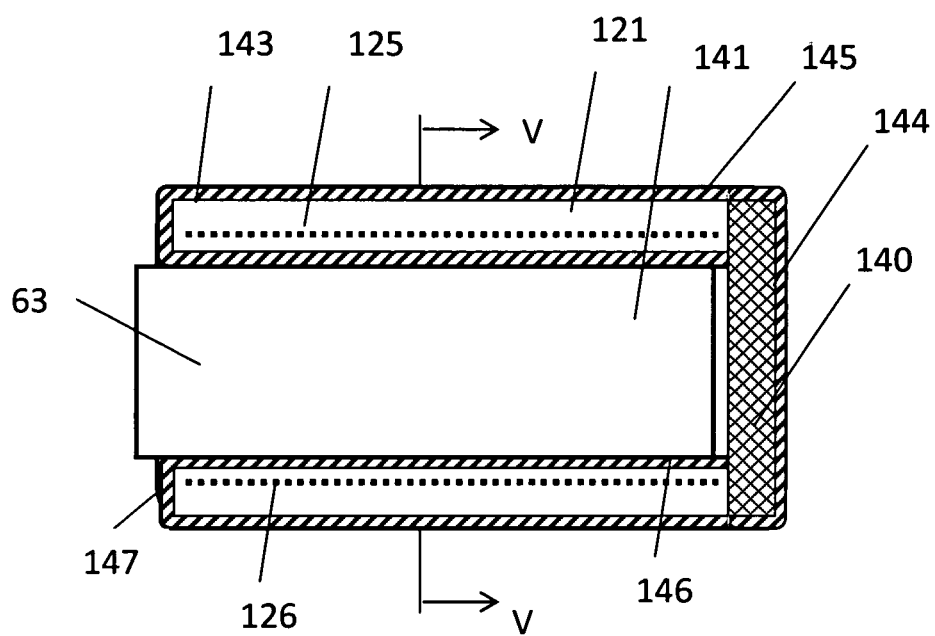
FIG. 58 is an enlarged cross section view taken along lines P-P of FIG. 50 with shown inserted member of a jaw of the instrument.

FIG. 56 is an enlarged cross section view taken along lines P-P of FIG. 50. FIG. 57 is an enlarged cross section view taken along lines O-O of FIG. 55. FIG. 58 is an enlarged cross section view taken along lines P-P of FIG. 50 with shown inserted member 63 of a jaw of the instrument. The cross section taken along lines V-V is the same as shown on FIG. 56.

Figure 59:
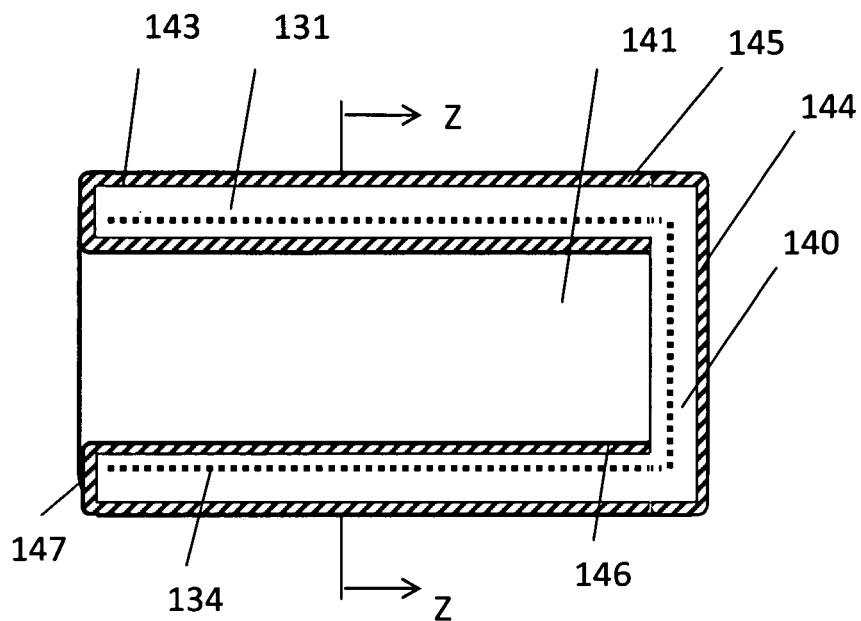
FIG. 59 is another enlarged cross section view taken along lines N-N of FIG. 51.

FIG. 59 is another enlarged cross section view taken along lines N-N of FIG. 51.

Figure 60:
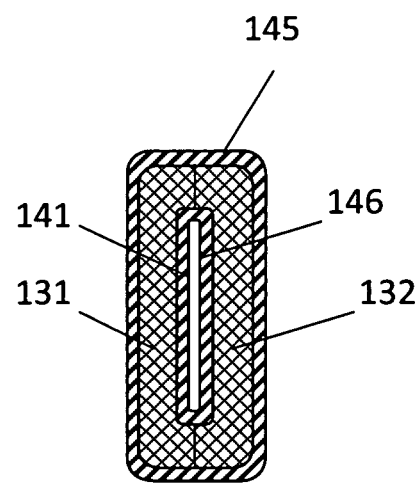
FIG. 60 is an enlarged cross section view taken along lines Z-Z of FIG. 59.

A tubular gauze is placed around cover 130. FIG. 60 is an enlarged cross section view taken along lines Z-Z of FIG. 50.

A tubular gauze can be placed around a different insert made of gauze, fabric or unwoven material. The tubular gauze eliminates the need to fold edges of the insert. A size of the tubular gauze is 10-22 mm, the most preferred size is 16 mm (⅝ in). The tubular gauze is elastic and covers the insert with the widths up to 1 in very well.

An insert can be made of elastic plastic materials as well. The preferred embodiment includes a cover with an insert made of gauze. A cover with described dimensions has the same volume as a 16 ply-10 cm×10 cm (4 in×4 in) surgical sponge. An occlusion instrument having two gauze covers provides not only an atraumatic occlusion but also absorbs the blood quickly keeping the zone of closing the uterus clean from the blood. As a result, the time for closing the uterus is shorten as well.

Figure 61:
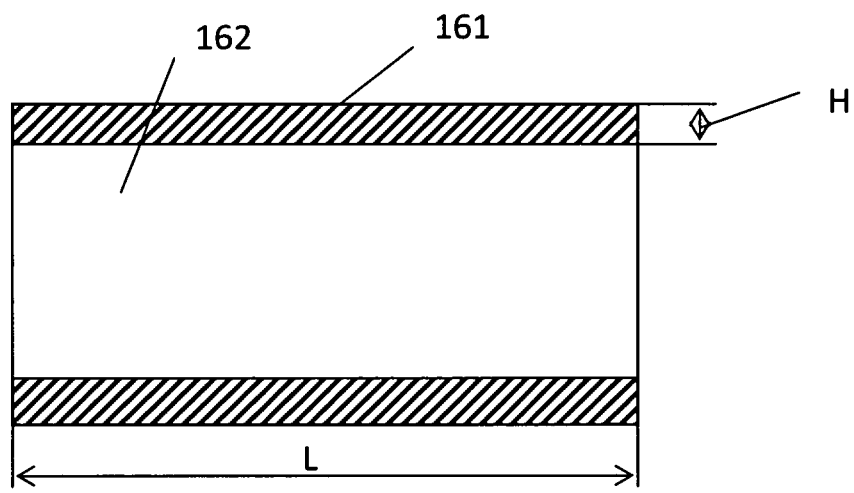
FIG. 61 depicts a cover made of rolled gauze.

FIG. 61 depicts a cover made of rolled gauze 161. The edges of the gauze are folded inside. The hole 162 is adjusted to receive a jaw of the clamp. The thickness H can be 3-15 mm, preferably, 5-10 mm. The wall of the cover 161 can be made of 16-50 layers of gauze, preferably 24-40 layers. The preferred length of the cover 161 is 50-60 mm. The width is about 10 to 30 mm, the preferred width is 12-25 mm.

Figure 62:
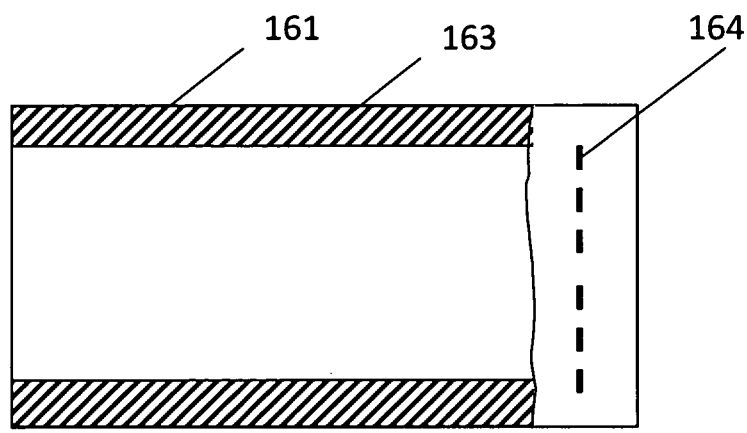
FIG. 62 depicts another cover made of rolled gauze.

FIG. 62 depicts cover 163 made of rolled gauze 161 by sewing its end. The seam 164 defines the thickness of the top of the cover.

Figure 63:
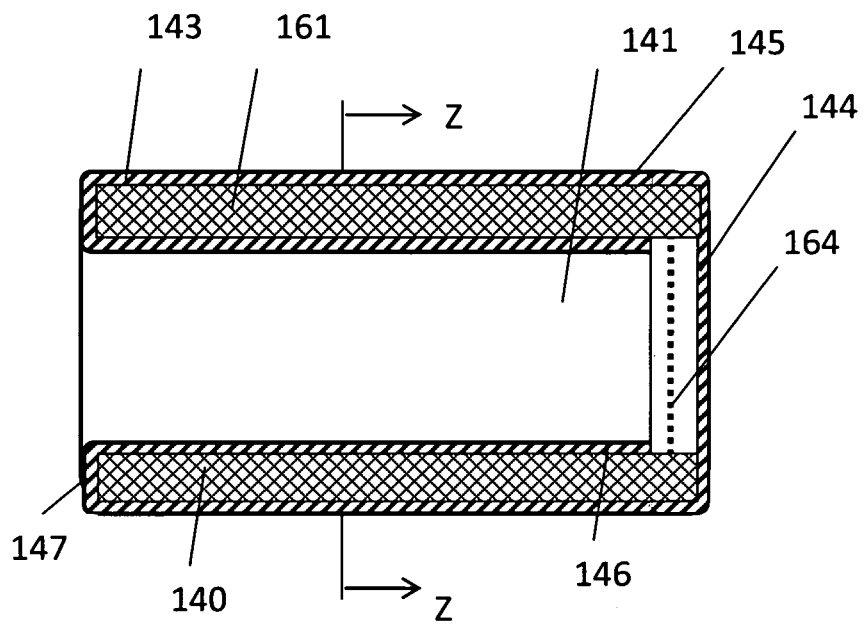
FIG. 63 is another enlarged cross section view taken along lines N-N of FIG. 51.

FIG. 63 is another enlarged cross section view taken along lines N-N of FIG. 51 with the cover 163 used as an insert. In this case the cover 163 can have edges unfolded.

Figure 64:
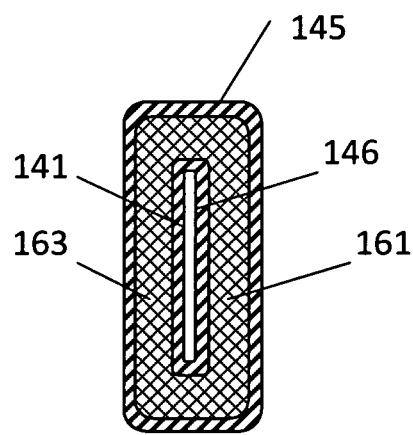
FIG. 64 is an enlarged cross section view taken along lines Y-Y of FIG. 63

FIG. 64 is an enlarged cross section view taken along lines Y-Y of FIG. 63

A cover can be used with a disposable instrument and with a reusable instrument. A covers might have a lace for additional securing the cover around a member of a jaw of a reusable instrument. A cover can be secured on a disposable instrument permanently, for example, by using an adhesive.

The instrument with the preferred thickness of the cover made of gauze creates a combination of the instrument and two surgical sponges. The blood draining capacity of the instrument eliminates the need for preliminary drainage of the blood of in the areas of occlusion of the arteries and, therefore, shortening the time needed in order to make the occlusions.

In addition, the covers provide sufficient drainage of the blood during the occlusion of the arteries.

The simplicity of application and removal of the clamp would allow any surgeon to use the clamp without prolong prior training and practice.

What is claimed is:

1. A surgical instrument for at least partial occlusion of the uterus blood vessels, comprising two opposing jaws with scissor-type handles and a latching mechanism, wherein the scissor-type handles are configured to maintain, at least, an open position and a working position, each jaw has a first straight member defining a flat working surface connected at an angle of 30 to 45 degrees relative to a second straight member and scissor-type handles, each said first straight member has a tubular cover, wherein each first straight member has a proximal portion having a proximal portion thickness and a distal portion having a distal portion thickness, and wherein the proximal portion thickness and the distal portion thickness are equivalent, each cover has a thickness, a width, a length, a radius, and a cavity having at least one side open from one end, wherein the cavity is configured to receive and retain the first straight member, and wherein the at least one side of the cavity is entirely enclosed within the cover, each said second straight member is integrated with said scissor-type handle, and wherein each second straight member has a second straight member inner side and a second straight member outer side, each jaw has a straight inner side and a straight outer side, wherein said jaws are made movable relative to one another, and wherein when the scissor-type handles are in the working position the straight inner sides are configured to touch and the second straight member inner sides are configured to touch, the latching mechanism is made to retain the jaws in the working position over a needed period of time and release the jaws when the need for occlusion is over, the thickness of each said cover on said inner side of said first straight member is 8-12 mm, the width of said cover is 10-30 mm, the length of said cover is 50-60 mm, the radius of said cover is 5-100 mm, and said cover is made of soft plastic, silicon, fabric, gauze, or non woven material.

2. A surgical instrument as in claim 1 configured to enable placement on an incision defining the patient's abdominal cavity while keeping the blood vessels atraumatically occluded.

3. A surgical instrument as in claim 1 in which the cover is made of two rectangular parts, the two parts being of equivalent length, each said part has two long sides, two short sides and a thickness, the parts are connected along the edges of both long sides and one short side creating a tube closed at one end and defining an inner cavity between said parts open from the other end of the tube for receiving and retaining the jaw, and wherein said parts are made of gauze or fabric.

4. A surgical instrument as in claim 3 in which the cover is made of a single piece of fabric or gauze.

5. A surgical instrument as in claim 1 in which the cover is made of a single piece of gauze.

6. A surgical instrument as in claim 1 in which the cover is covered by a bag made of a piece of tubular gauze, having two ends with edges, one end of the tubular gauze is closed and the other end of the tubular gauze is open defining an inner space of the bag for receiving and retaining the jaw, the edges of the closed end are folded inside the bag and the edge of the open end are folded inside the bag or inside the inner cavity of the cover.

7. A surgical instrument as in claim 1 which includes a lace attached to the cover and said lace is adjusted for securing the cover to the jaw.

8. A surgical instrument as in claim 1 in which at least the side of the cover to be engaged with the blood vessels has at least one one-piece insert along its length made of silicon, gauze or fabric.

9. A surgical instrument for at least partial occlusion of the uterus blood vessels, comprising two opposing jaws with scissor-type handles and a latching mechanism, each jaw has a first straight member defining a flat working surface connected at an angle of 30 to 45 degrees relative to a second straight member and scissor-type handles, each said first straight member has a tubular cover, each cover has a thickness, a width, a length, a radius, and a cavity open from one end, the cavity having at least one side, wherein the cavity is configured to receive and retain the first straight member, wherein the at least one side of the cavity is entirely enclosed within the cover, wherein at least the side of the cover to be engaged with the blood vessels has a plurality of inner holes, wherein the holes run parallel to the side of the cover to be engaged with the blood vessels, each said second straight member is integrated with said scissor-type handle, each jaw has a straight inner side and a straight outer side, wherein said jaws are made movable relative to one another in order to at least partially and atraumatically occlude the uterus blood vessels by clamping directly onto such uterus blood vessels as exposed in an abdominal cavity over the course of uterine surgery by opposing sides of the covers on the inner sides of the first straight members, the latching mechanism is made to retain the jaws in a working position over a needed period of time and release the jaws when the need for occlusion is over, the thickness of each said cover on said inner side of said first straight member is 8-12 mm, the width of said cover is 10-30 mm, the length of said cover is 50-60 mm, and the radius of said cover is 5-100 mm.

10. The surgical instrument of claim 9, wherein said cover is made of soft plastic, silicon, fabric, gauze, or non-woven material.

* * * * *